United States Patent
Hashimoto et al.

(10) Patent No.: US 6,245,017 B1
(45) Date of Patent: Jun. 12, 2001

(54) 3D ULTRASONIC DIAGNOSTIC APPARATUS

(75) Inventors: Shinichi Hashimoto; Yasuhiko Abe; Yoichi Ogasawara; Hitoshi Yamagata, all of Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/429,902

(22) Filed: Oct. 29, 1999

(30) Foreign Application Priority Data

Oct. 30, 1998 (JP) .................................................. 10-311367
Nov. 6, 1998 (JP) .................................................. 10-316584

(51) Int. Cl.$^7$ ...................................................... A61B 8/00
(52) U.S. Cl. ............................................ 600/447; 128/916
(58) Field of Search ..................................... 600/443, 447, 600/445, 456, 472; 73/625, 626, 606; 367/7, 11, 130; 128/916

(56) References Cited

U.S. PATENT DOCUMENTS

| | | | |
|---|---|---|---|
| 4,559,952 | * 12/1985 | Angelsen et al. | 600/472 |
| 4,596,145 | 6/1986 | Smith et al. . | |
| 5,485,842 | * 1/1996 | Quistgaard | 600/443 |
| 5,497,776 | * 3/1996 | Yamazaki et al. | 600/445 |
| 5,546,807 | 8/1996 | Oxaal et al. . | |
| 5,720,291 | * 2/1998 | Schwartz | 600/456 |
| 5,993,391 | * 11/1999 | Kamiyama | 600/443 |

OTHER PUBLICATIONS

E. D. Light, et al. "Progress in Two–Dimensional Arrays for Real–Time Volumetric Imaging", Ultrasonic Imaging, vol. 20, 1998, pp. 1–15.

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

A three-dimensional ultrasonic diagnostic apparatus includes a two-dimensional array type of ultrasonic probe. A three-dimensional scan operation of scanning a three-dimensional region within a human body under examination with ultrasound and a two-dimensional scan operation of scanning a two-dimensional plane within the three-dimensional region with ultrasound are selectively performed by a beam former unit. Under the control of a controller, the three-dimensional scan operation is repeated intermittently and the two-dimensional scan operation is repeated during the interval between each three-dimensional scan. Three-dimensional ultrasonic image data concerning the three-dimensional region is produced on the basis of received echo signals obtained by the three-dimensional scan operation. Two-dimensional ultrasonic image data concerning the two-dimensional plane section is produced on the basis of received echo signals obtained by the two-dimensional scan operation.

26 Claims, 18 Drawing Sheets

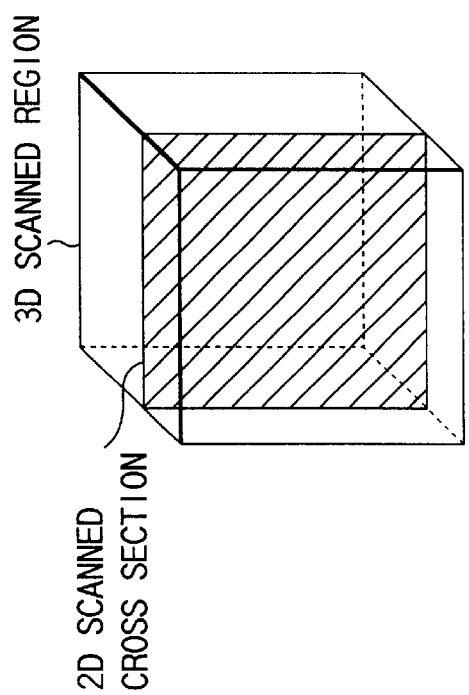
FIG. 8A
FIG. 8B
FIG. 8C
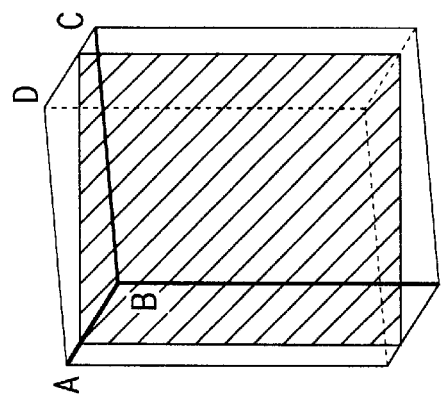
FIG. 9B
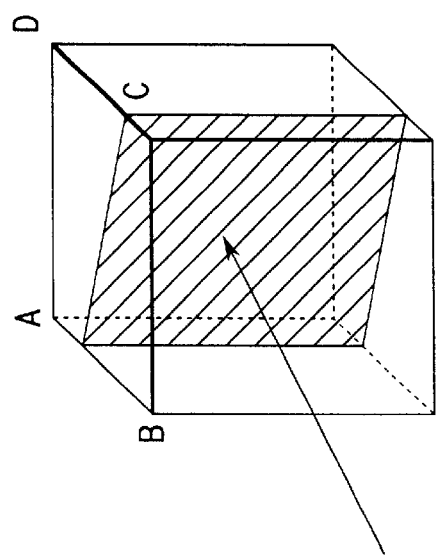
FIG. 9A

α-CROSS
SECTION

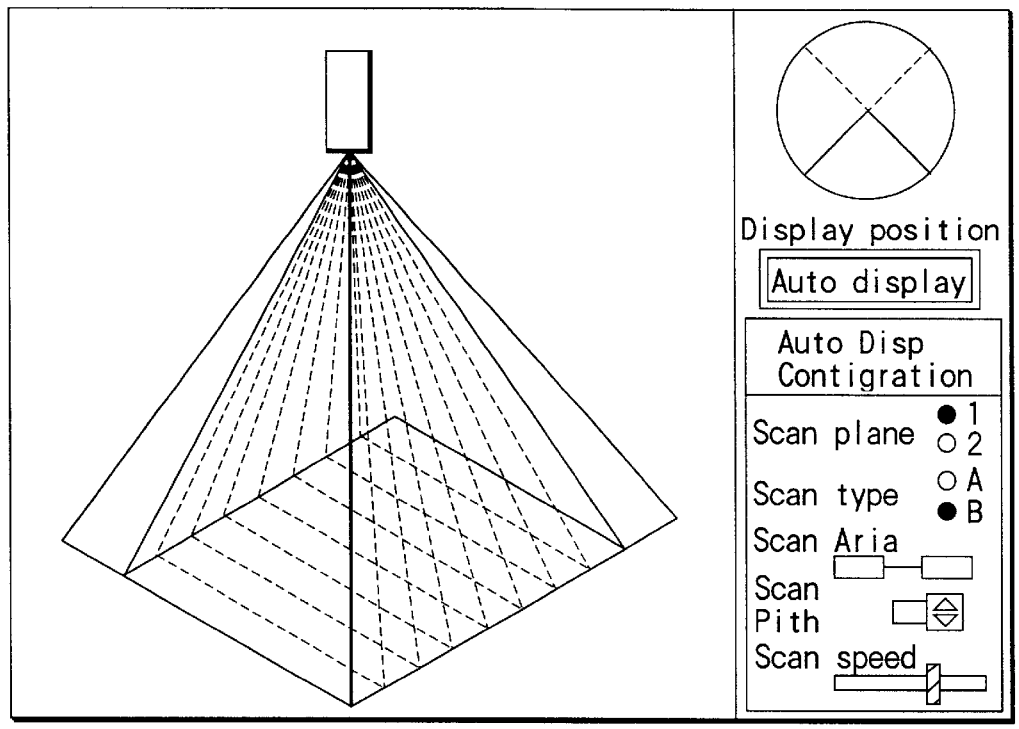
FIG. 15A
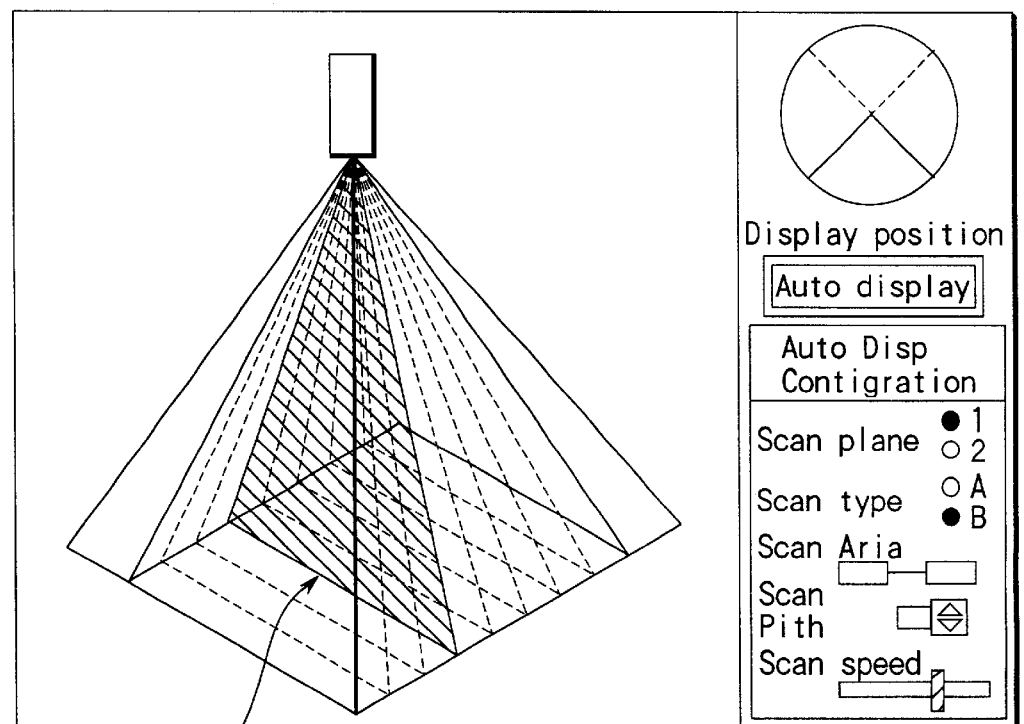
α-CROSS
SECTION       FIG. 15B (1) PROBE MODEL
    (A-MARK, B-MARK)
(2) WIRE FRAME MODEL OF 3D REGION
(3) 2D IMAGE
    (A-PLANE)
(4) 2D IMAGE
    (B-PLANE)

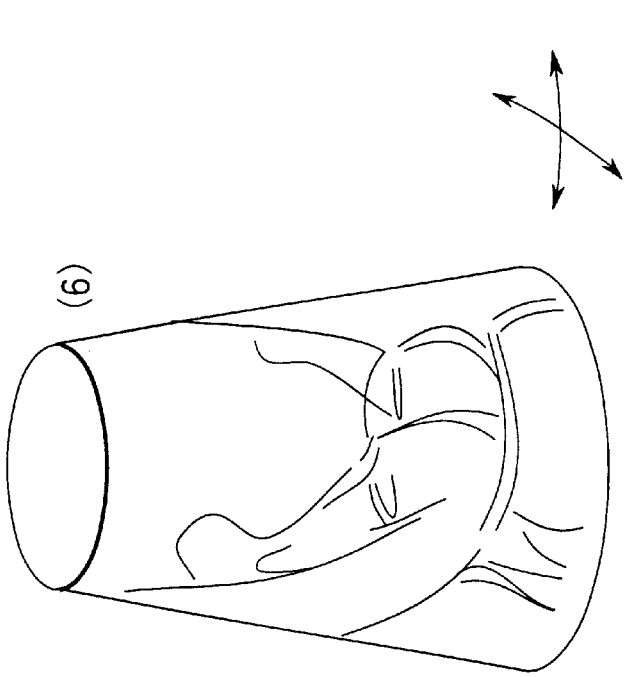
(1) PROBE MODEL
(2) WIRE FRAME MODEL OF 3D REGION IN FIRST SCANNING MODE (INCLUDE CROSS SECTION FRAME)
(5) WIRE FRAME MODEL OF 3D-ROI
(6) 3D IMAGE OF 3D-ROI
FIG. 17B (ROTATION)
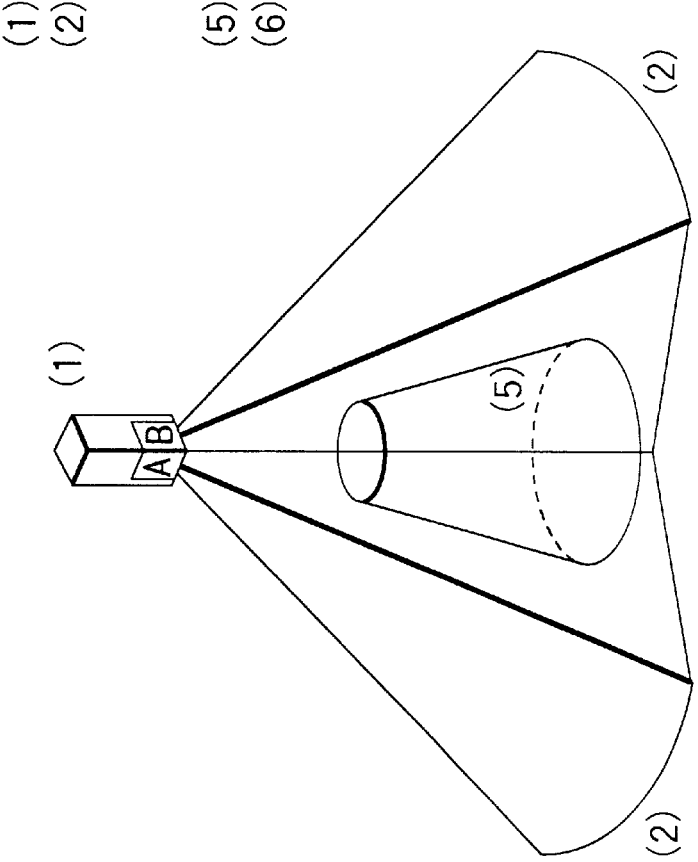
FIG. 17A

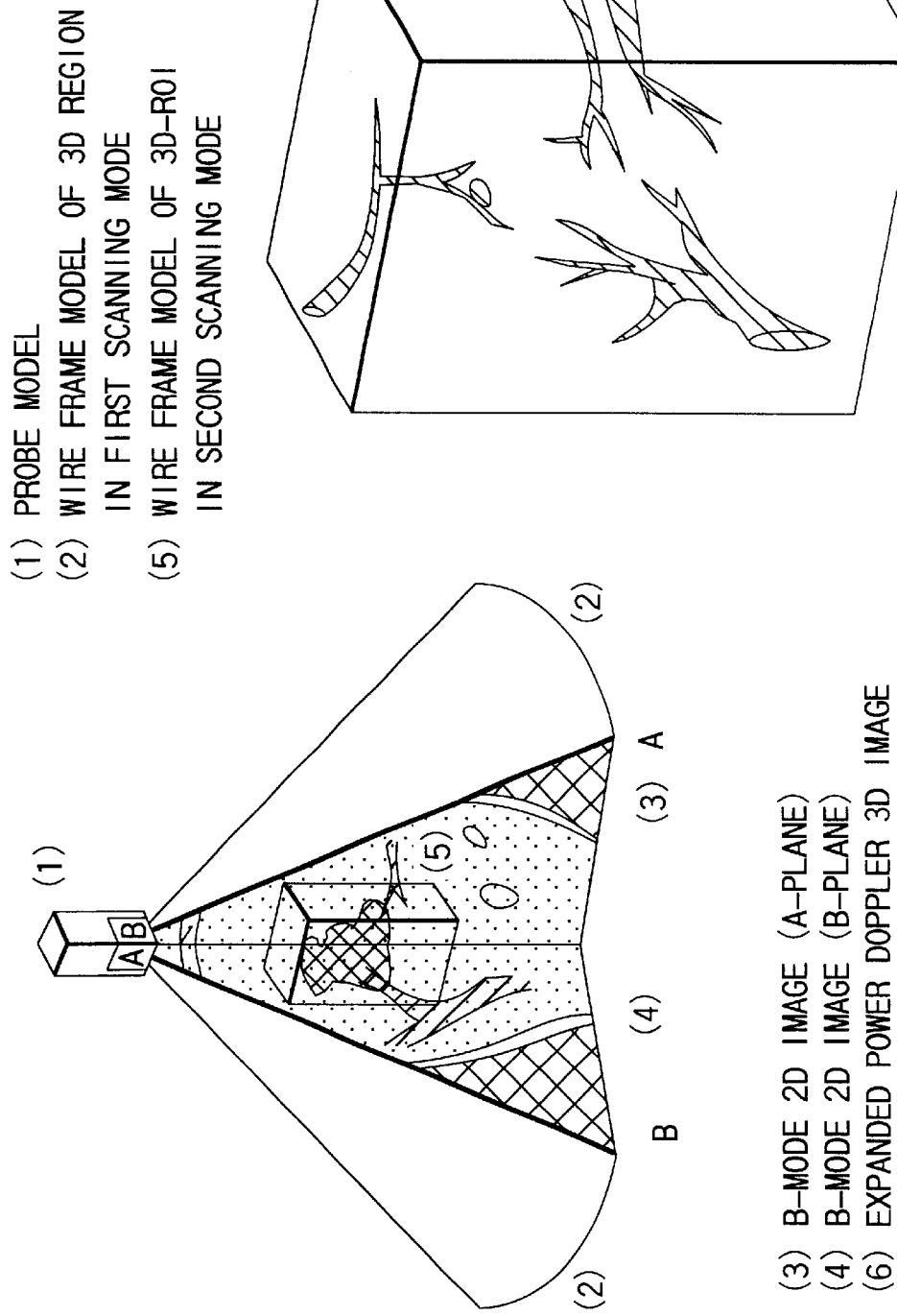

FIG. 21A BASIC CASE
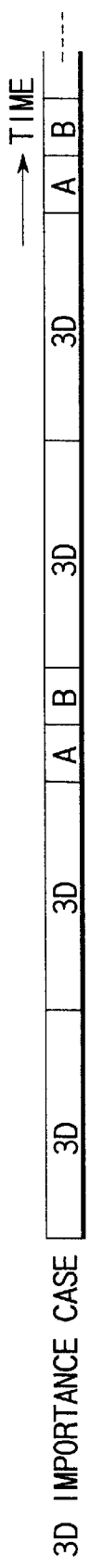
FIG. 21B 3D IMPORTANCE CASE
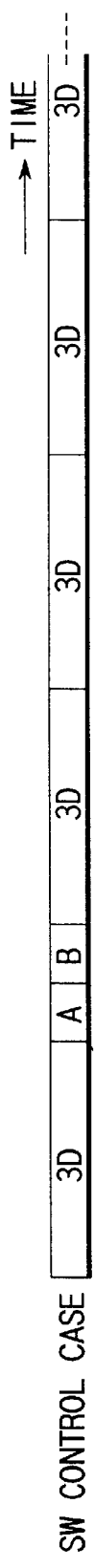
FIG. 21C SW CONTROL CASE
FIG. 21D 2D IMPORTANCE CASE
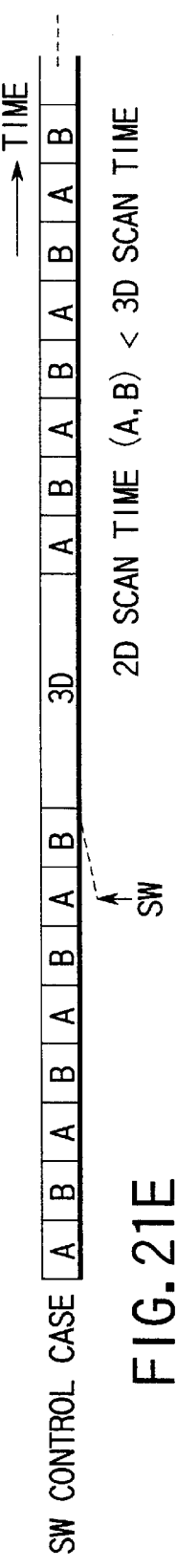
FIG. 21E SW CONTROL CASE

3D ULTRASONIC DIAGNOSTIC APPARATUS

BACKGROUND OF THE INVENTION

The present invention relates to a 3D (three-dimensional) ultrasonic diagnostic apparatus which visualizes a 3D region within a human body under examination and more specifically to a technique for improving the real-time imaging.

This application is based on Japanese Patent Application No. 10-311367 filed on Oct. 30, 1998 and Japanese Patent Application No. 10-316584 filed on Nov. 6, 1998, the entire content of which is incorporated herein by reference.

Recent 2D types of ultrasonic probes can scan a 3D region within a human body under examination with ultrasound to produce a 3D image. This type of scanning is referred to as 3D scanning or volume scanning. Whereas conventional 2D scanning is required only to move ultrasound along a plane section of a human body, the 3D scanning needs to move ultrasound in all directions within a 3D region of the human body. In order to reproduce natural movements of internal organs in real time, it is required to reduce the time required to scan the 3D region thoroughly for the purpose of improving temporal resolution (volume rate). That is, it is required to set the number of times that the 3D region is scanned every second to about 30 times per second as in the 2D scanning.

As is well known, the velocity of propagation of ultrasound through human body is nearly constant; therefore, the number of times per unit time that ultrasound is transmitted and received is limited. That is, since the time required for transmission and reception of an ultrasound beam is absolutely determined by the depth of field and the ultrasound propagation velocity, the transmission/reception rate is almost fixed.

In order to satisfy the real-time requirements of the 3D scanning, therefore, it is required to reduce the spatial resolution (the density of ultrasound scanning lines). In order to increase the number of ultrasound scanning lines per second, the adoption of a simultaneous reception scheme known as digital beam forming has been considered. However, even with the digital beam forming, echoes are only received from some directions at most for each transmission, resulting in a failure to gain sufficient spatial resolution. It might be expected to increase the spatial resolution by increasing the number of directions from which echoes are received simultaneously. However, this approach would require applied energy to be considerably high and therefore might cause damage to the array probe and fail to meet safety standards.

The ultrasonic 3D imaging method, as its typical operation, extracts concerned parts from 2D image data obtained, and superimposes the extracted concerned parts one on another to create a 3D image. In this method, therefore, part of 2D image data drops off.

Further, it is very useful in diagnosis to display a tissue image (B-mode image) and a blood-flow image (color Doppler image) in combination. However, the 3D representation capability is still being improved.

With the ultrasonic imaging, although its imaging range is narrower than the imaging range of X-ray computerized tomography apparatus and magnetic-resonance imaging apparatus, . . . This causes a problem in that it is difficult for an observer to understand the orientation and position of a 3D image in a human body under examination.

BRIEF SUMMARY OF THE INVENTION

It is an object of the present invention to provide a 3D ultrasonic diagnostic apparatus which permits the compatibility of the attainment of relatively high spatial and temporal resolution with the provision of 3D image information.

The three-dimensional ultrasonic diagnostic apparatus of the present invention has an arrangement required to repeat a three-dimensional scan operation of scanning a three-dimensional region within a human body under examination intermittently with ultrasound and to repeat a two-dimensional scan operation of scanning a two-dimensional plane section within the three-dimensional region with ultrasound during the interval between each three-dimensional scan.

The three-dimensional ultrasonic diagnostic apparatus of the present invention has an arrangement required to scan two two-dimensional plane sections within a three-dimensionally scannable three-dimensional region with ultrasound and to display two images concerning the two plane sections in combination according to their positional relationship so that internal three-dimensional structure can be estimated.

Additional objects and advantages of the invention will be set forth in the description which follows, and in part will be obvious from the description, or may be learned by practice of the invention. The objects and advantages of the invention may be realized and obtained by means of the instrumentalities and combination particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 8A schematically shows an initial position relationship between the 3D scan region and the 2D scan plane section in the first embodiment;

FIG. 8B schematically shows a parallel movement operation of the 2D scan plane section relative to the 3D scan region in the first embodiment;

FIG. 8C schematically shows a slanting operation of the 2D scan plane section with respect to the 3D scan region in the first embodiment;

FIGS. 9A and 9B schematically show the displacement of the point of view to compensate for the slant view of the 2D image shown in FIG. 8C;

FIG. 15A shows changes of the display screen when an operation of parallel-shifting automatically the 2D scan plane section is performed in the second embodiment;

FIG. 15B shows the third cross section α in second embodiment;

FIG. 17A shows a location map for representing the position of a truncated cone-shaped 3D scan local region in a 3D scan region in the second embodiment;

FIG. 17B shows a 3D image displayed within the 3D scan local region in FIG. 17A;

FIG. 19A shows a location map for a rectangular parallelepiped-shaped 3D scan local region for Doppler imaging in the second embodiment;

FIG. 19B shows a 3D image displayed within the 3D scan local region in FIG. 19A;

FIGS. 21A through 21E show variations of alternate scanning between 2D and 3D in the second embodiment.

DETAILED DESCRIPTION OF THE INVENTION

Hereinafter, the preferred embodiments of three-dimensional ultrasonic diagnostic apparatus of the present invention will be described in detail with reference to the accompanying drawings. In the description below, "three-dimensional" and "two-dimensional" are abbreviated to 3D and 2D, respectively.

[First Embodiment]

Figure 1:
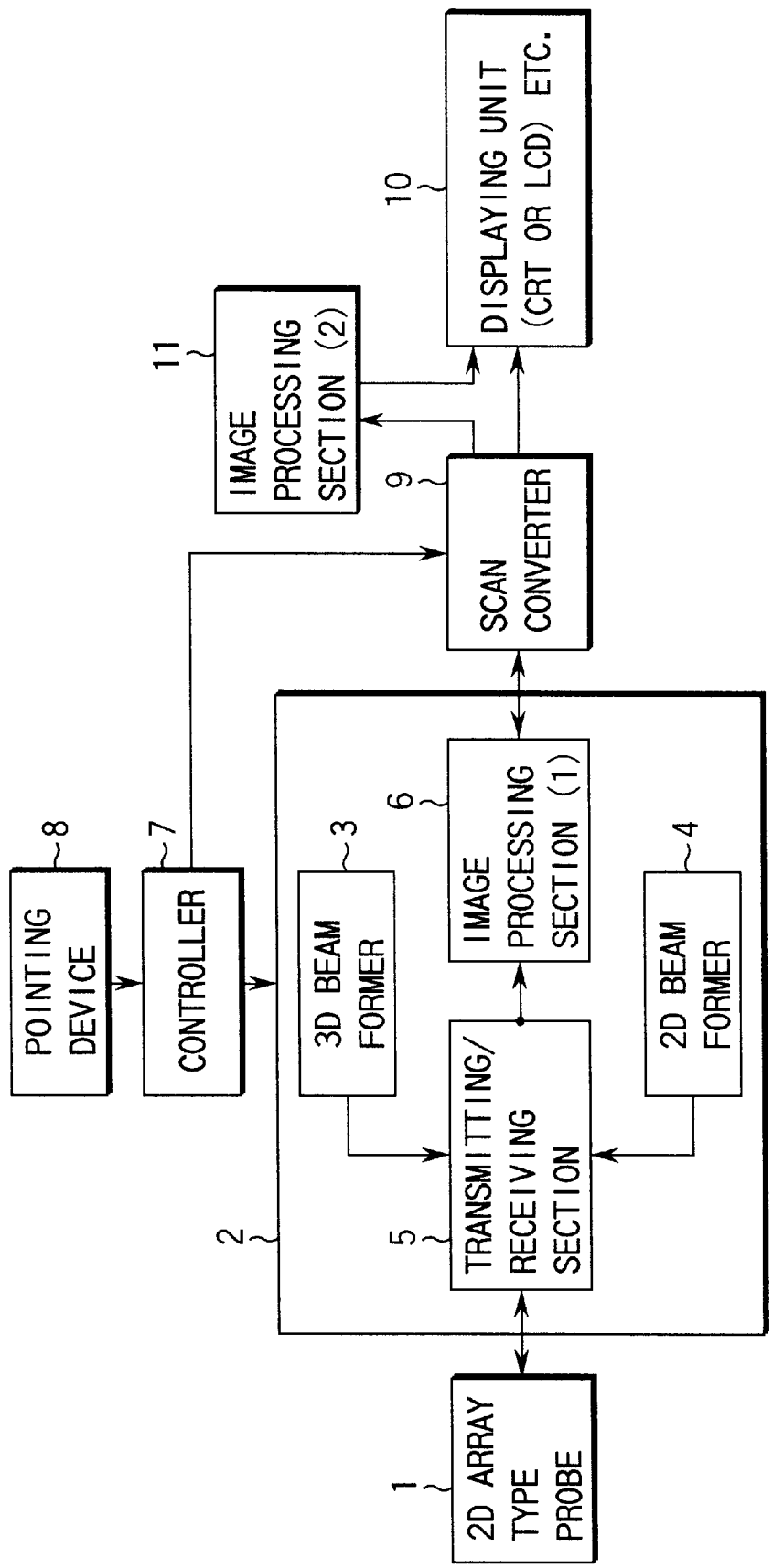
FIG. 1 is a block diagram of a 3D ultrasonic diagnostic apparatus according to a first embodiment of the present invention.

Referring now to FIG. 1, there is illustrated in block diagram form a 3D ultrasonic diagnostic apparatus according to a first embodiment of the present invention. In FIG. 1, a 2D array ultrasonic probe 1 has a number of piezoelectric elements each formed on top and bottom with electrodes. The piezoelectric elements are arranged in a 2D array.

To the ultrasonic probe 1 is connected an image gathering and processing unit 2, which has a 3D beam former 3 that performs on a transmitter/receiver section 5 delay control required to scan a 3D region within a human body under examination with ultrasound through the probe 1 and a 2D beam former 4 that performs on the transmitter/receiver section 5 delay control required to scan a plane section within the 3D region with ultrasound through the probe 1. The 2D beam former and the 3D beam former are separated functionally for the sake of description but in practice they are implemented in the same hardware. The image gathering and processing unit 2 has an image processing section (1) 6 that produces 2D image data, such as B-mode image data, on the basis of received echo signals from the transmitter/receiver section 5 based on the 2D scan and produces 3D image data on the basis of the outputs of the transmitter/receiver section 5 for the 3D scan.

The position of a plane section to be subjected to a 2D scan is initially set at the center of the 3D region.

A scan converter 9 is provided to combine the 2D image data and the 3D image data produced by the image gathering and processing unit 2 into one frame of image data and convert the resulting composite image data into a video signal format. The composite image data is displayed on a display unit 10 such as a cathode ray tube (CRT) or liquid crystal display (LCD). The scan converter 9 has a function of converting non-isotropic 3D image data which is obtained by the sector scanning method, which will be later described, into isotropic 3D image data. Therefore, in the case of the sector scanning method in particular, the apparatus is, in some cases, equipped with an image processing unit (2) 11 for generating 3D image data by processing 3D image data from the scan converter 9. A controller 7 has control of the entire ultrasonic diagnostic apparatus. A pointing device 8, such as a mouse, a trackball, or a keyboard, is connected to the controller 7 in order to allow an operator to enter various commands.

Figure 2:
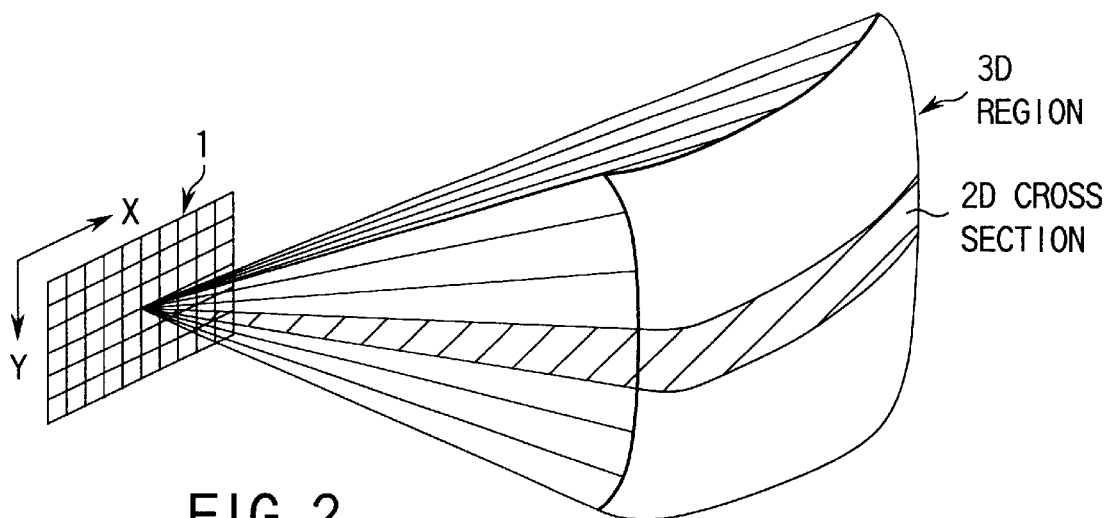
FIG. 2 schematically shows the position of a 2D scan plane section relative to a 3D scan region based on sector scan in the first embodiment.
Figure 3:
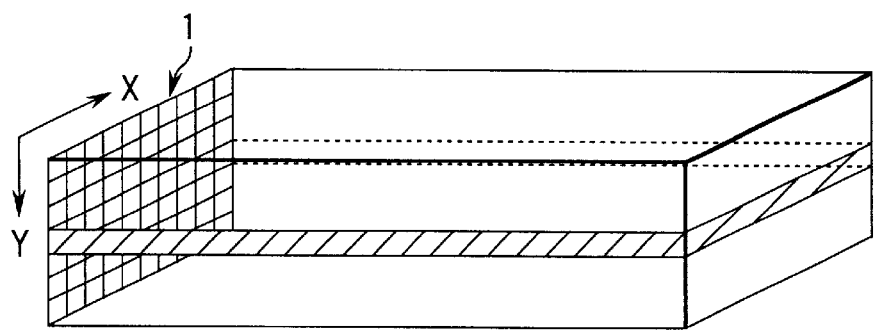
FIG. 3 schematically shows the position of a 2D scan plane section relative to a 3D scan region based on linear scan in the first embodiment.
Figure 4:
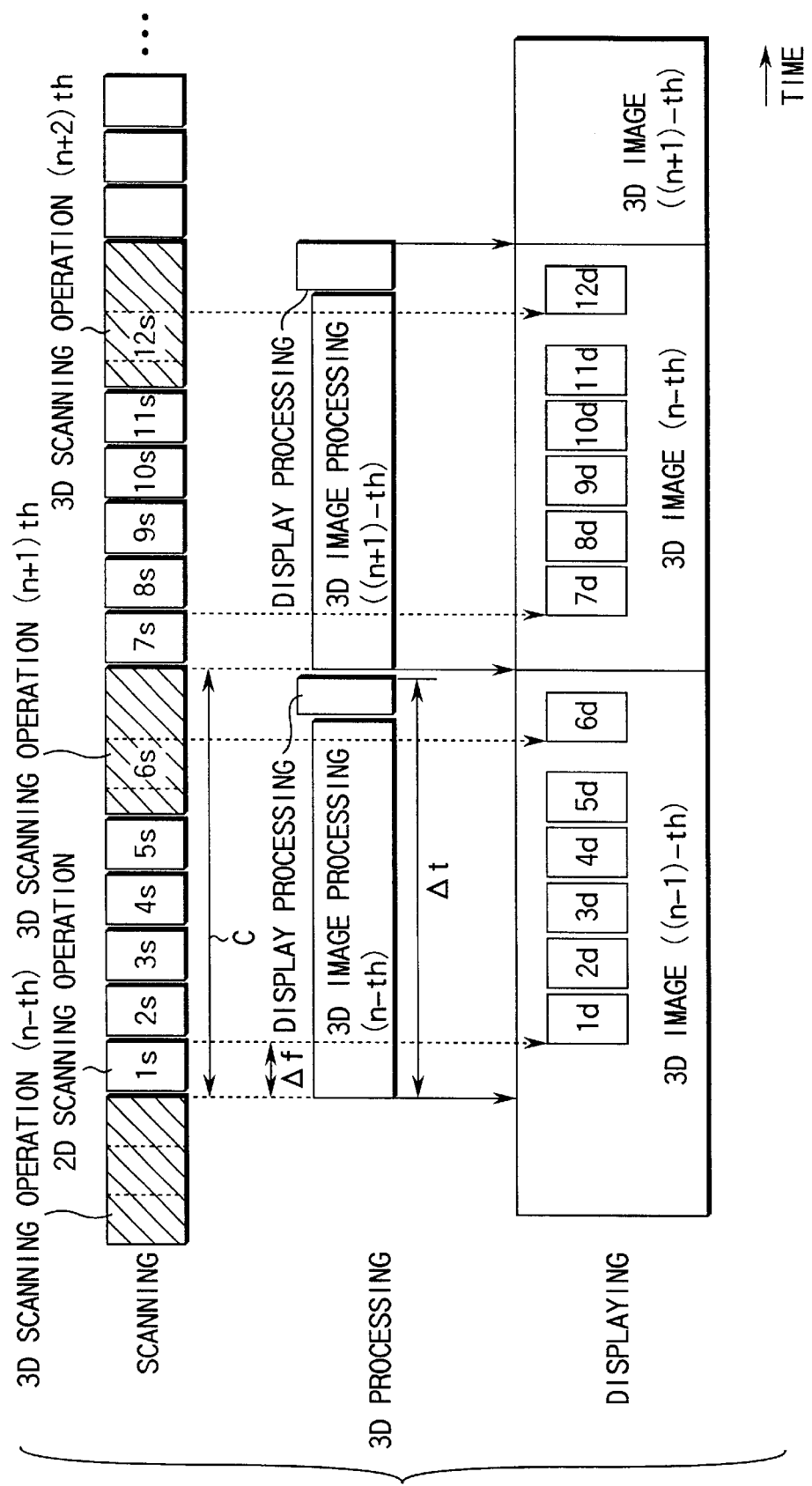
FIG. 4 illustrates 2D scanning, 3D scanning, 3D processing, 2D image display, and 3D image display in the first embodiment.

The operation of the 3D ultrasonic diagnostic apparatus thus arranged will be described below. In this embodiment, sector scan, linear scan or any other scan can be used. In FIG. 2, there is illustrated a 3D region and a 2D plane section (indicated hatched) each subjected to sector scan. In FIG. 3, there is illustrated a 3D region and a 2D plane section (indicated hatched) each subjected to linear scan. In FIG. 4, there is illustrated mixed scan of 3D scan of the 3D region shown in FIGS. 2 or 3 with ultrasound and 2D scan of the 2D plane section within the 3D region with ultrasound. The 3D scan is made repeatedly but intermittently. During the interval between each 3D scan, the 2D scan is repeated. As a typical case, a 2D scanning frame rate (the number of times of scanning cross sections per 1 second) is sufficiently higher (more frequent) than a 3D scanning volume rate (the number of times of scanning 3D regions per 1 second). In the 3-dimensional scanning operation, a so-called parallel simultaneous signal receiving mode which generates a plurality of ultrasonic echo signals in the signal receiving direction per one ultrasonic signal reception, is employed. It should be noted here that generally, the parallel simultaneous signal receiving mode is not employed in the 2-dimensional scanning operation. However, the parallel simultaneous signal receiving mode may be employed in the 2-dimensional scanning operation. In this case, the number of signals received in the parallel simultaneous mode for the 2-dimensional scanning operation (the number of ultrasonic echo signals generated per one ultrasonic signal reception) is set lower than the number of signals received in the parallel simultaneous mode for the 3-dimensional scanning operation.

The period C of the 3D scan operation is set equal to or longer than the length of time required by 3D processing and display processing, i.e., the time Δt between the moment that a 3D scan is terminated and the moment that 3D image data is produced. Thereby, a delay of 3D image display with respect to the progress of the 3D scan operation is compensated for and 3D images can be displayed one after another at the period C of the 3D scan operation.

The image processing section (1) 6 or (2) 11 employs general 3D image processing such as volume rendering or MIP to produce 3D image data one after another at the period C from received signals gathered by each 3D scan. The resulting 3D image data are displayed in succession after another at the display period equal to the 3D scan period C.

The image processing section in the image gathering and processing unit 2 produces 2D image data one after another at time intervals of ΔT required for each 2D scan from received signals gathered by each 2D scan as shown in FIG. 4. The resulting 2D image data are displayed one after another at the display period equal to the 2D scan period ΔT.

While a 3D scan is being made, no 2D scan is carried out and hence no 2D image data is produced. Therefore, the 2D image display is interrupted temporarily, failing to display the motion of an organism smoothly. However, this embodiment compensates for the effects of the temporal interruption of 2D image display by producing and displaying 2D image data concerning the plane section which is an object of the 2D scan operation on the basis of a portion of received signals gathered by a 3D scan.

The 3D image data are displayed on the same screen as the 2D image data while being switched at the same period C as the 3D scan operation. The 3D image data and the 2D image data may be displayed on separate portions of the same screen. Alternatively, the 2D image data may be displayed superimposed upon the 3D image data according to its position in the 3D region.

Figure 5:
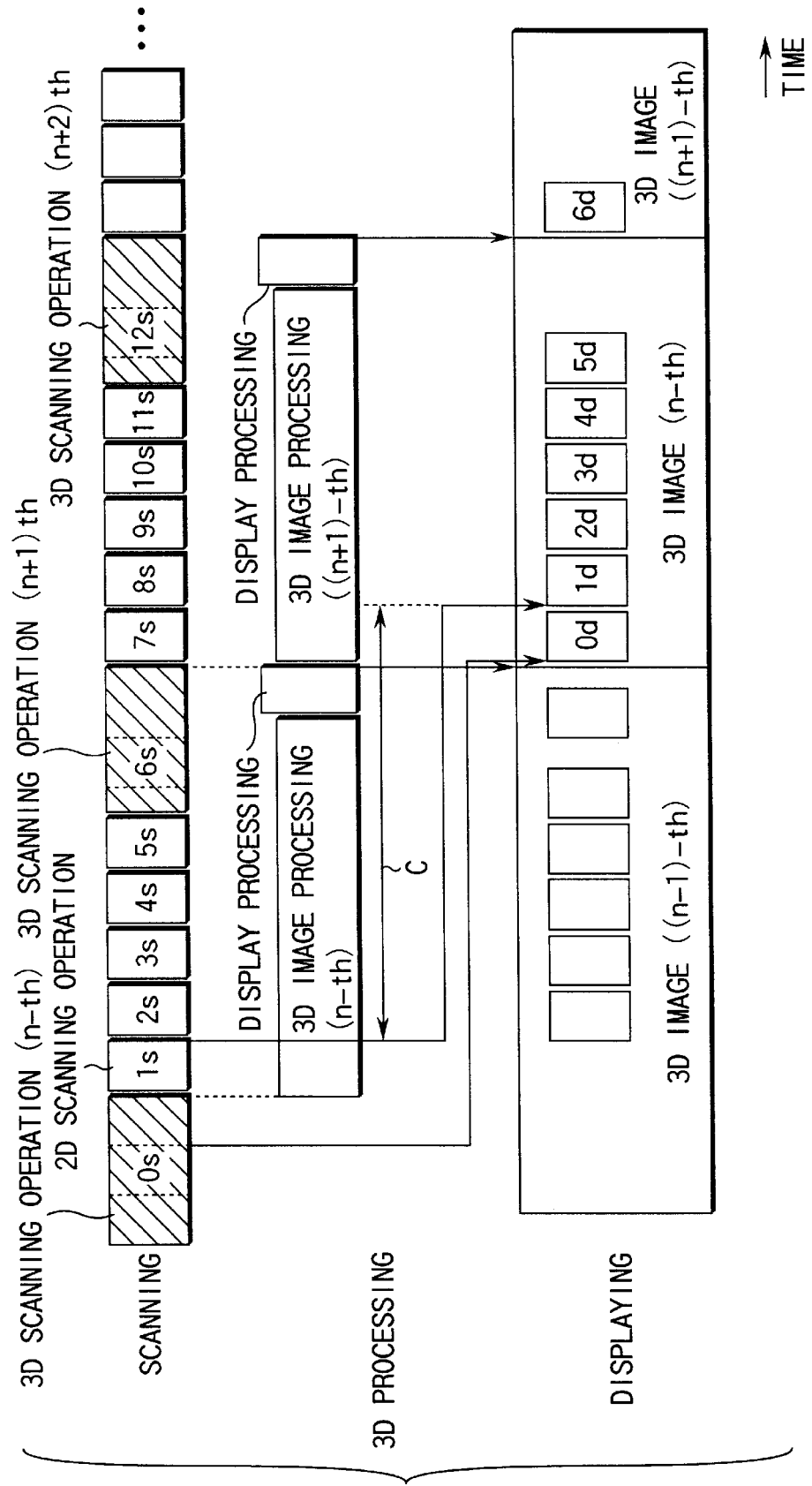
FIG. 5 shows a modification of the 2D image display of FIG. 4.

Here, since the time Δt required by 3D processing and display processing is very longer than the time ΔT for 2D processing and display processing, the timing of displaying 3D image data is delayed considerably with respect to the display of 2D image data. To compensate for that delay, as shown in FIG. 5, the reading of 2D image data from the scan converter 9 may be delayed by the time C which elapses from the termination of a 3D scan to the time when 3D image data is produced.

Figure 6:
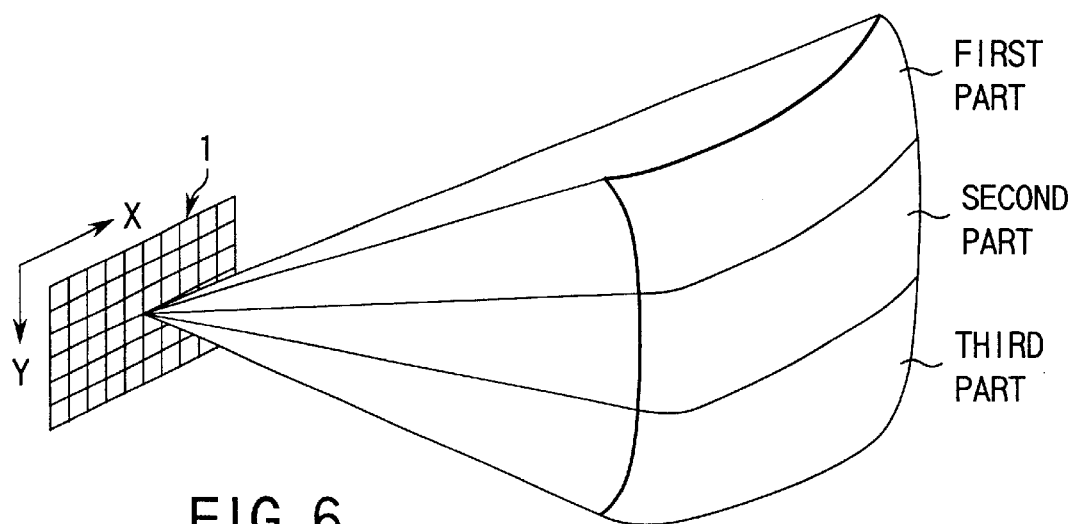
FIG. 6 schematically shows three parts that form the 3D scan region in the first embodiment.
Figure 7:
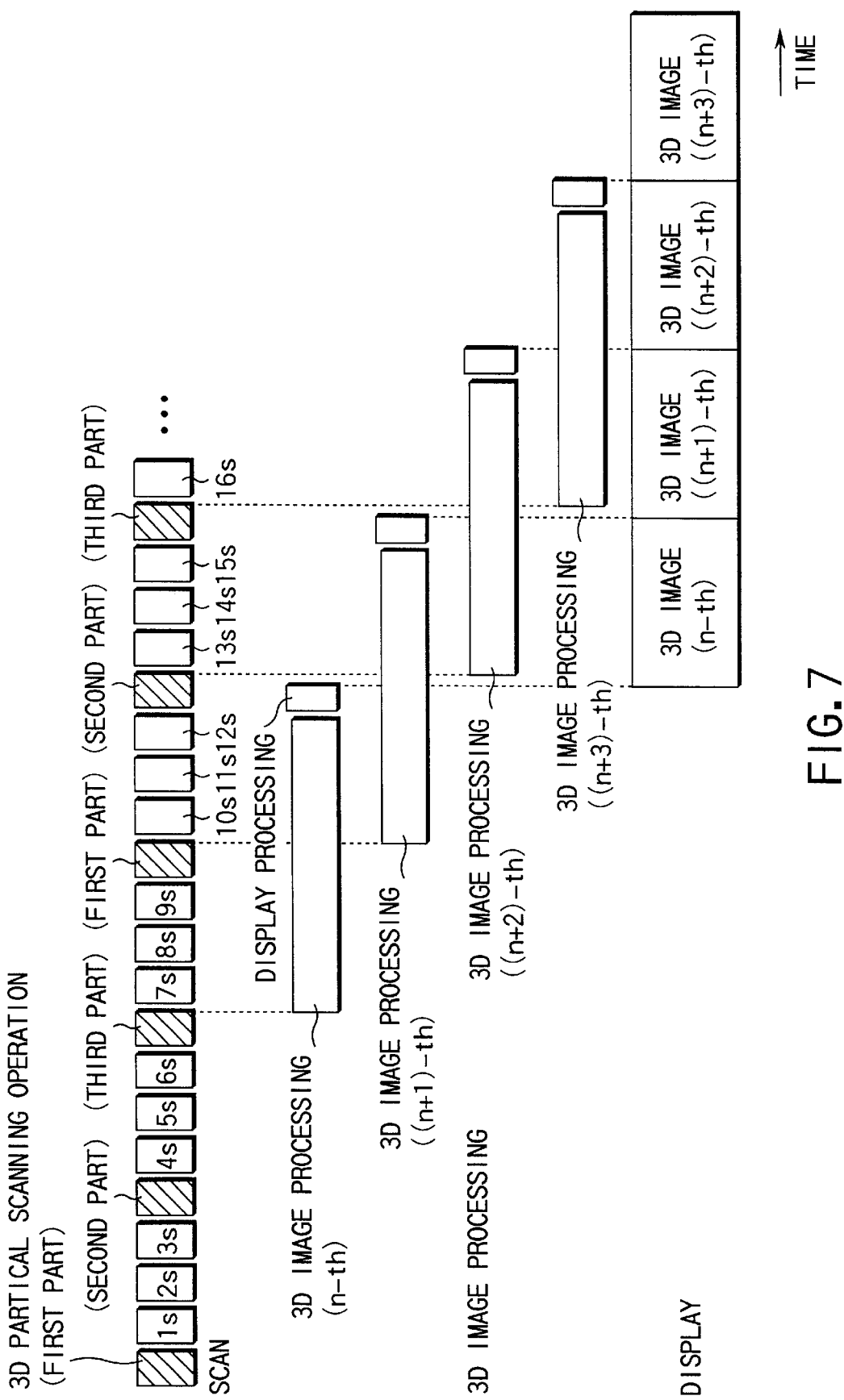
FIG. 7 illustrates 2D scanning, 3D scanning, 3D processing, 2D image display, and 3D image display for the three parts shown in FIG. 6.

The aforementioned 3D scan operation can be modified as follows. FIG. 6 shows three subregions that make up a 3D region. As shown in FIG. 7, a 3D subscan operation of scanning the first subregion, a 3D subscan operation of scanning the second subregion and a 3D subscan operation of scanning the third subregion are carried out in this sequence at regular intervals. In other words, the 3D subscan operation is repeated intermittently and a separate 3D subregion is scanned for each 3D subscan operation. According to such a 3D scan approach, 3D image data concerning a 3D region is produced by three successive 3D subscan operations. Thus, the period at which 3D image data is produced can be shortened to improve the temporal resolution of a 3D image. Alternatively, the spatial resolution of 3D image data can be improved with the period at which 3D image data is produced maintained.

As stated previously, the location of a plane section subjected to 2D scan is initially set at the center of a 3D region. The operator can operate the pointing device 8 to parallel shift the plane section any distance within the 3D region as shown in FIGS. 8A and 8B or to slant the plane section at an angle with respect to the 3D region as shown in FIG. 8C. The operator can perform this operation prior to scan or during scan while viewing the image.

Thus, if the 2D plane section is slanted with the direction of view fixed, then the operator will have to view the 2D image at an angle. This may sometimes make it difficult to view the image. For this reason, as shown in FIGS. 9A and 9B, the image processing section 6 is arranged to shift the point of view for 3D processing onto the center line of the slanted plane section and then change the direction of view to conform to that center line. As a result, the 2D image will always be displayed as a front image and the 3D image will look as if it has been rotated in the direction opposite to the direction in which the plane section was slanted.

As obvious from the above description, since this embodiment repeats a 3D scan operation and repeats a 2D scan operation during the interval between each 3D scan, the 3D structure of an organism of a human body under examination can be observed from a 3D image and internal movement can be observed through a 2D image with high temporal resolution. In addition, since the driving energy per unit time to the probe 1 can be made lower than in the case where the 3D scan operation alone is repeated in succession, the possibility of damage to the probe can be reduced and the safety of the probe can therefore be improved.

[Second Embodiment]

Figure 10:
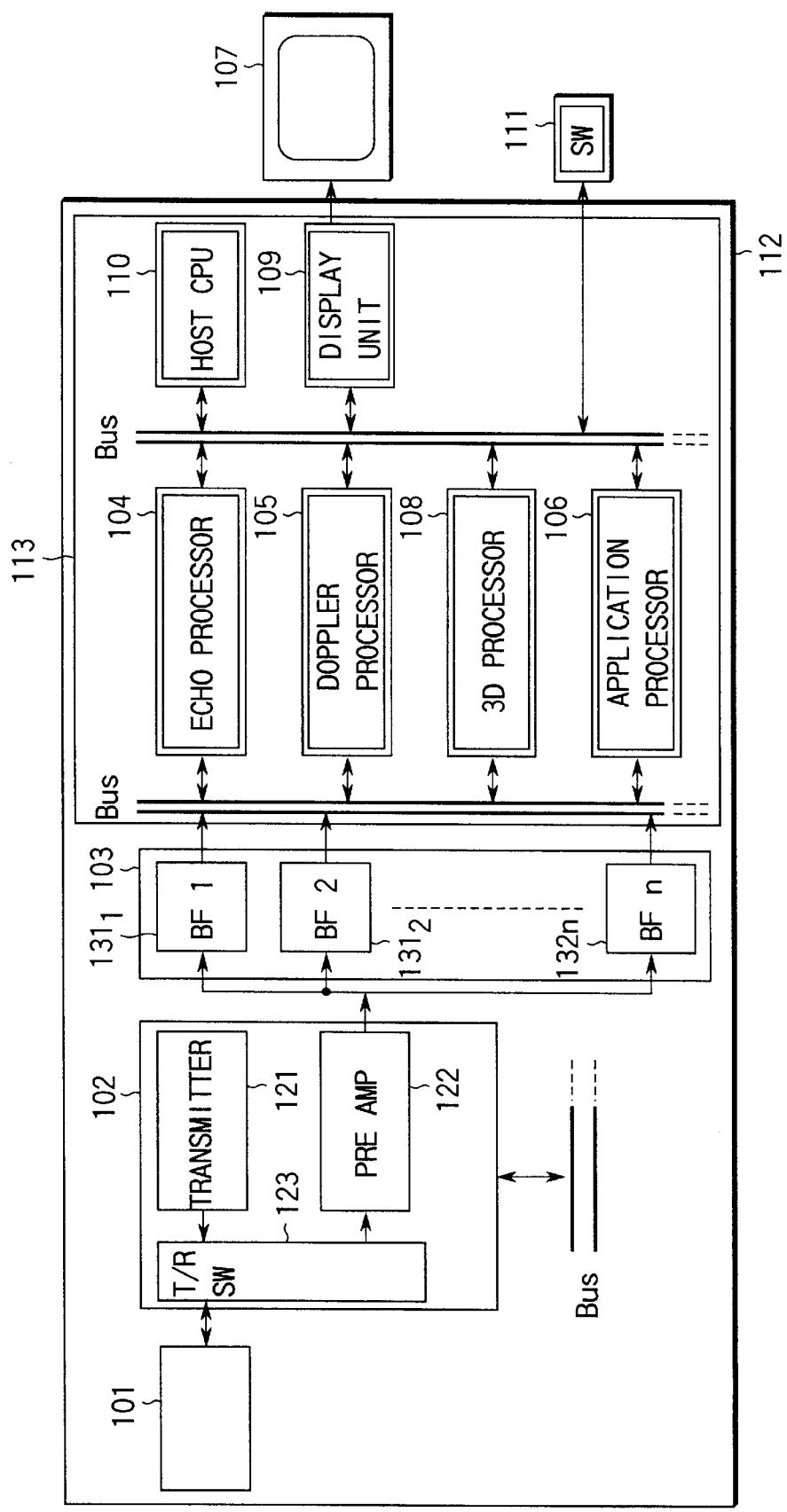
FIG. 10 is a block diagram of an ultrasonic diagnostic apparatus according to a second embodiment of the present invention.

FIG. 10 schematically shows an ultrasonic diagnostic apparatus according to a second embodiment of the present invention. This apparatus is composed of an ultrasonic probe 101, an apparatus body 112, a display unit 107, and a scan panel 111. The ultrasonic probe 101 used is of a 2D array type in which a number of piezoelectric elements adapted for inter-conversion between electric and acoustic signals are arranged in a matrix.

The apparatus body 112 is constructed from a transmitter/receiver unit 102, a digital beam former switch unit 103, an image processing unit 113, a host CPU 110, and a display unit 109. The transmitter/receiver unit 102 comprises a transmission/reception switch 123 for switching between transmission and reception, a transmitter 121, and a preamplifier 122. The switch 123, at the time of transmitting ultrasound, connects the transmitter 121 to the ultrasonic probe 101 and, at the time of receiving echoes, connects the preamplifier 122 to the ultrasonic probe.

The transmitter 121, which is comprised, through not shown, of a clock generator, a frequency divider, a transmission delay circuit, and a pulser, converts clock pulses from the clock generator to rate pulses of, say, 6 KHz through the frequency divider, then applies the rate pulses through the delay control circuit to the pulser to produce high-frequency voltage pulses and drives the piezoelectric elements with the voltage pulses. Namely, the piezoelectric elements are subjected to mechanical vibrations to produce ultrasound. The ultrasound thus produced is reflected by acoustic impedance boundaries within the human body back to the ultrasonic probe 101, thus subjecting the piezoelectric element to mechanical vibrations. An electrical echo signal is thus produced individually in each piezoelectric element. The resulting electrical echo signals are amplified in the preamplifier 122 and then sent to a beam former unit 103 where they are added in phase. In this way, signals having directivity (received echo signals) are produced.

The diameter of a beam of ultrasound is increased intentionally by delay control of voltage pulses to the piezoelectric elements. This is intended to reduce the time required to scan through a 3D region within a human body under examination with ultrasound, i.e., the time required by a 3D scan (also referred to as a volume scan), and thereby improve the temporal resolution, i.e., the number of times per second that the 3D region is scanned, or the volume rate and increase the real-time operability. In order to produce a plurality of (n in this example) received signals differing in directivity each time a large-diameter beam of ultrasound is transmitted, that is, in order to implement multidirectional simultaneous reception, the digital beam former unit 103 is equipped with a plurality of (n in this example) digital beam formers 131-1 to 131-n each of which is arranged to sum received echo signals in phase at a different time.

The image processing unit 113 is equipped with four processors 104, 105, 106, and 108 which are connected with a bus. The application processor 106 has a processing facility mainly required for display and measurement. An echo processor 104 is responsive to received signals from the digital beam former unit 103 to produce B-mode image data that provides morphological information of tissues (information about the structure and form of tissues). The echo processor 104 extracts from the received signals harmonic components having frequencies that are integral multiples of the fundamental frequency and then produces tissue harmonic image data that is capable of providing the morphological information of tissues more clearly.

A unit that implement the so-called color flow mapping (CFM), the Doppler processor 105 is arranged to subject the received echo signals from the digital beam former unit 103 to quadrature detection to derive a frequency-shifted Doppler signal, cause specific frequency components in the resulting Doppler signal to pass through an MTI (moving target indicator) filter, determine the frequencies that passed through the filter by the use of an autocorrelator, and compute average velocity, variance, and power. By adjusting the passband of the MTI filter, general CFM image data that mainly visualize tissues and blood-flow velocity and tissue Doppler image data that mainly visualize the tissue shapes of cardiac muscles and the like can be produced selectively. In addition, the Doppler processor is capable of producing power Doppler image data from the power that visualize the shape of tissues and blood flow.

The 3D processor 108 is arranged to produce 3D-like image data as will be described later from any of the B-mode image data, the tissue harmonic image data, the CFM image data, the tissue Doppler image data, and the power Doppler image data.

In addition, the 3D processor 108 can form a simple graphic, such as a wire-frame model, that represents the contour of a 3D scan region within a human body under examination. The 3D processor can execute processing required to implement various display modes such as of superimposing B-mode image data upon that wire-frame model. Image data produced by the 3D processor is displayed through the display unit 109 upon the display screen 107.

[Basic Scanning and 3D-like Display Screen Configuration]

Figures 11A, 11B:
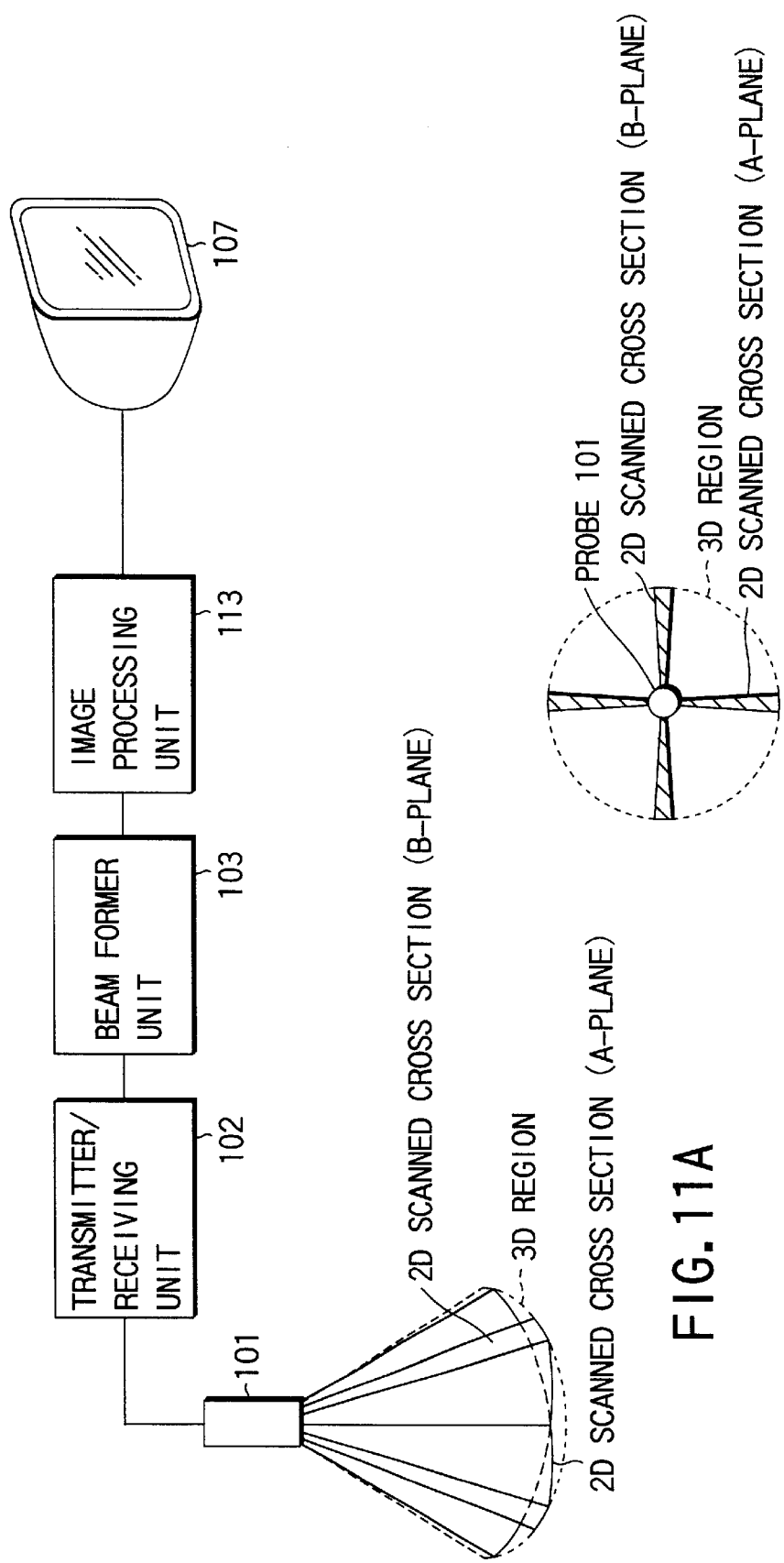
FIG. 11A shows in perspective the positions of two 2D scan plane sections relative to a 3D scan region in the second embodiment.
FIG. 11B is a plan view illustrating the positions of the two 2D scan plane sections relative to the 3D scan region in the second embodiment.
Figure 12:
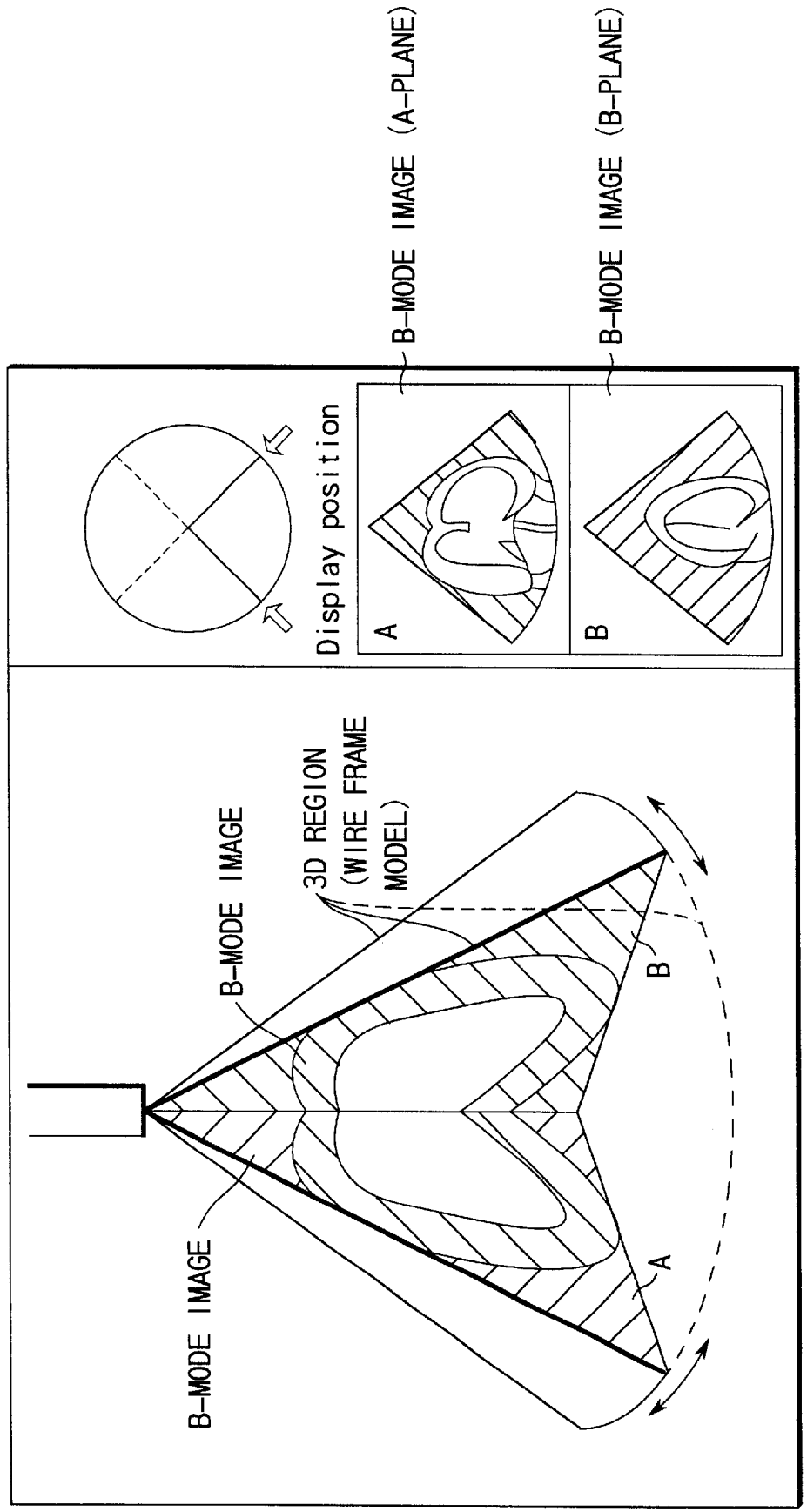
FIG. 12 shows a basic display screen in the second embodiment.

In the present embodiment, the key to the operation of displaying tomography data, such as B-mode image data, in a 3D-like fashion is to display schematically a 3D region that can be scanned with ultrasound using a wire-frame model with its vertex at the ultrasound emitting surface of the ultrasonic probe 101 as shown in FIG. 11A. Two plane sections A and B within the 3D region that meet at a point on the center axis of the ultrasonic probe 101 are alternately subjected to a 2D scan. The resulting tomography data for those two plane sections are superimposed on the wire frame model with registration as shown in FIG. 12. In this registration, the two 2D-scan cross-sectional images are fitted accurately in their respective positions on the wire frame model. At the lower right of the display screen each of the two 2D-scan cross-sectional images is separately displayed in full as a B-mode image.

To facilitate the understanding of the positional relationship between two plane sections to be 2D scanned and set easily such two plane sections, a 3D region guide figure as viewed from the probe side is displayed at the upper right of the display screen. By operating on the guide figure with the pointing device on the scan panel 111, two plane sections can be changed or shifted. When the plane sections are changed, the conditions under which the probe 101 is driven by the transmitter/receiver unit 102 are changed accordingly, whereby the 2D scan plane sections are changed automatically.

Figure 13:
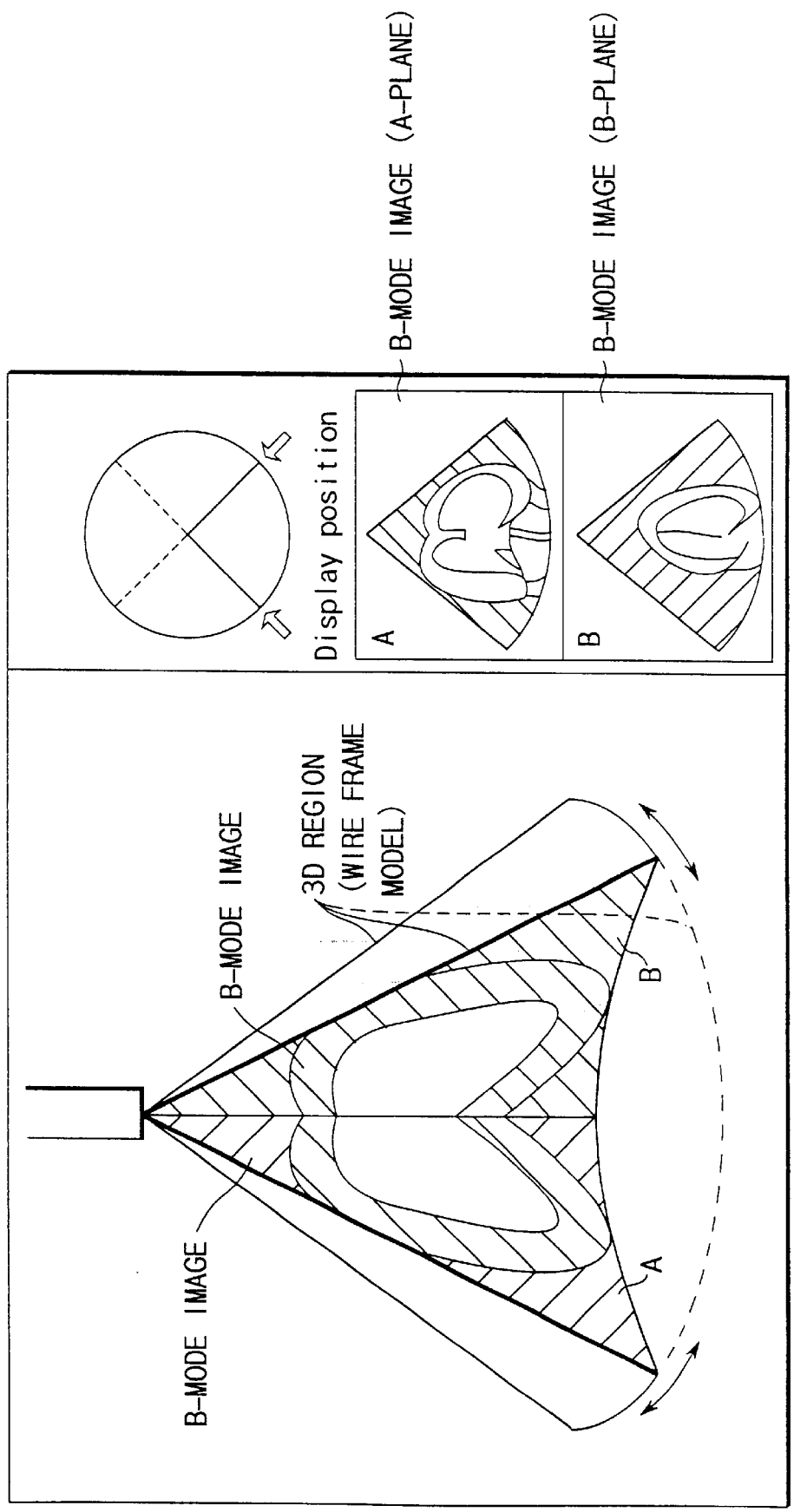
FIG. 13 shows a display screen when a convex 2D scan is made in the second embodiment.

The 2D plane sections may be curved as shown in FIG. 13. This scan can be made by changing delay times regularly not only for the azimuth direction in which ultrasound is directed but also the direction normal to the azimuth direction each time ultrasound is transmitted.

According to the present embodiment, as described above, sine only two plane sections within a 3D region are scanned with ultrasound, under the same temporal resolution the density of ultrasound scan lines can be improved significantly as compared with the case where the 3D region is scanned in its entirety, whereby high spatial resolution, that is, high image quality is attained. In addition, since the two tomography images for the two plane sections that meet are combined in such a way as to conform to their actual position and then registered with and fitted in the wire-frame model that schematically represents the 3D region, morphological 3D information can be recognized by intuition in comparison with the case where the two tomography images are simply displayed in a line. Furthermore, by shifting the two plane sections manually, the structure and form of tissues and the blood flow can be understood well in a 3D-like fashion.

Although, in the above description, only two plane sections are subjected to 2D scan, this is not restrictive. Three or more plane sections may be subjected to 2D scan within some temporal and spatial resolution tolerance.

[Automatic Shifting of Plane Section]

Automatic shifting of at least one of the two plane sections allows the further promotion of the understanding of the structure and form of tissues and the blood flow in a 3D-like fashion. FIGS. 14A, 14B, 15A and 15B illustrate display examples. At the lower right of the display screen is displayed a menu for setting up automatic shifting conditions. On the menu, the plane to be shifted automatically can be specified to be either A plane or B plane. The scan scheme can be specified to be either type a or type b. The range over which the plane is to be shifted can be specified in terms of an angle. The pitch at which the plane is shifted can be specified. The speed at which the plane is shifted can be specified. The transmitter/receiver unit 102 automatically shifts the selected plane to be subjected to 2D scan in accordance with the automatic shifting conditions thus set and the display unit 110 displays the resulting tomography images one after another in the wire frame model.

Figure 14A:
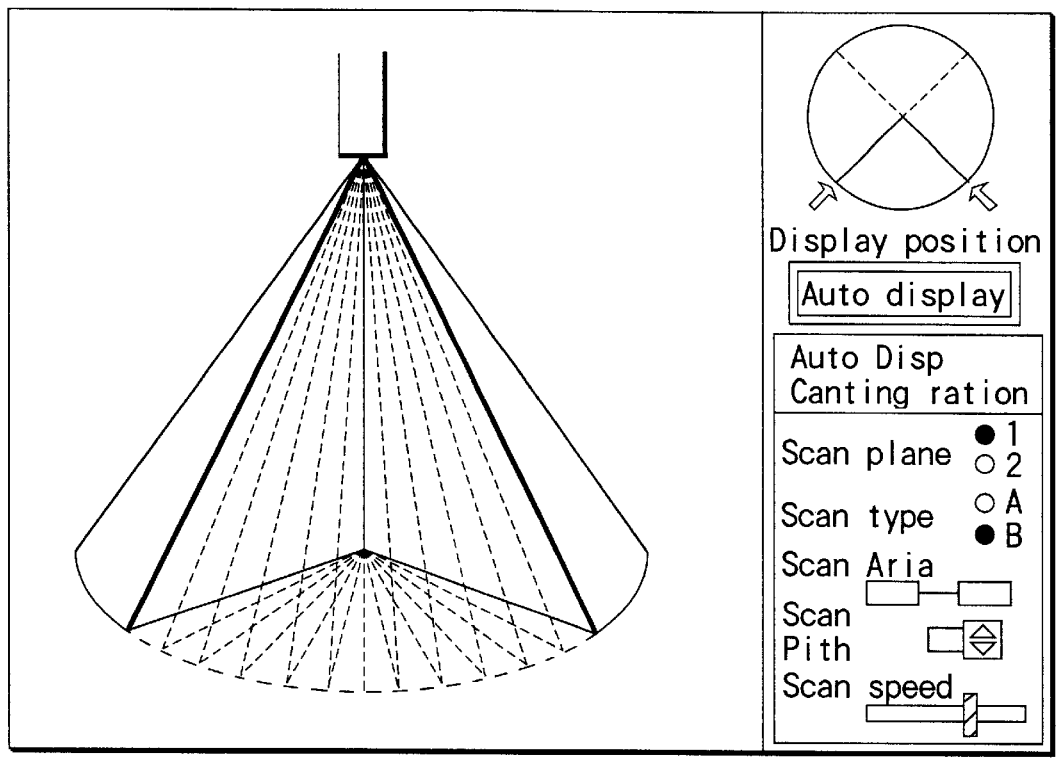
FIG. 14A shows changes of the display screen when an operation of rotating automatically the 2D scan plane section is performed in the second embodiment.
Figure 14B:
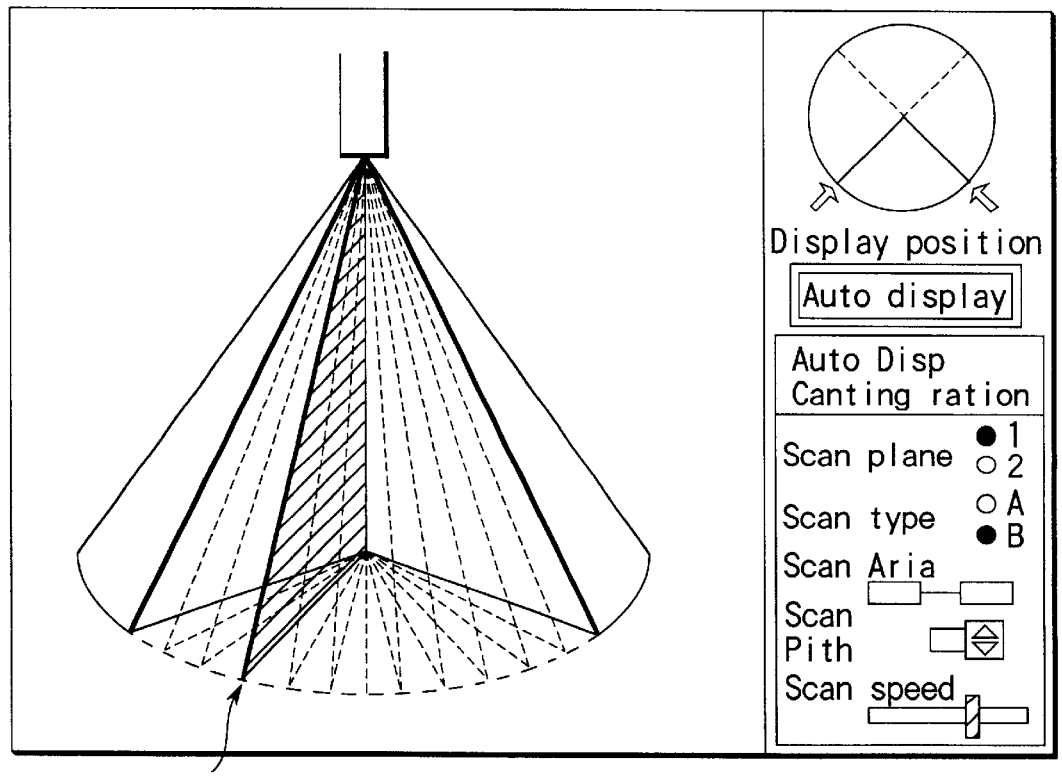
FIG. 14B shows the third cross section α in second embodiment.

FIG. 14A illustrates the manner in which the selected plane is shifted in accordance with the scan type a. In the scan type a, the plane is rotated automatically with the center axis of the 3D region as the center of rotation. In FIG. 15A, there is illustrated the manner in which the selected plane is shifted in accordance with the scan type b, in which case the plane is shifted along the direction perpendicular to it.

With such automatic shifting of a plane section, after the ultrasonic probe 101 is applied to the human body surface, two plane sections that pass through the center axis of a 3D region are displayed in real time (a live image or a moving image), and, upon depression of the automatic shift button, one of the plane sections is shifted through the 3D region and the resulting tomography images are displayed one after another within a wire frame model indicating the 3D region. The selected plane section can be selectively shifted in one direction only or in two directions.

The plane sections to be shifted are not limited to the two plane sections A and B. An additional plane section α to be scanned may be set as shown in FIGS. 14A or 15B. For example, if the plane section α is set at the boundary between the plane sections A and B, then the area to be observed will become easy to recognize as a whole. When the plane section α is being shifted and displayed, both the plane sections A and B may be displayed in the form of either live images or still images, which are switched as required by means of switches or the like. In the case where the plane sections A and B are displayed in the form of still image, only the plane section α is scanned, that allowing the temporal and spatial resolution to be prevented from lowering.

Next, the specific operation of the ultrasonic diagnostic apparatus of this embodiment will be described. The apparatus can be selectively operated in three scan modes. The aforementioned display of FIG. 12 forms the basis for any of the three scan modes. The three scan modes will be explained below in sequence.

[First Scan Mode]

Figure 16:
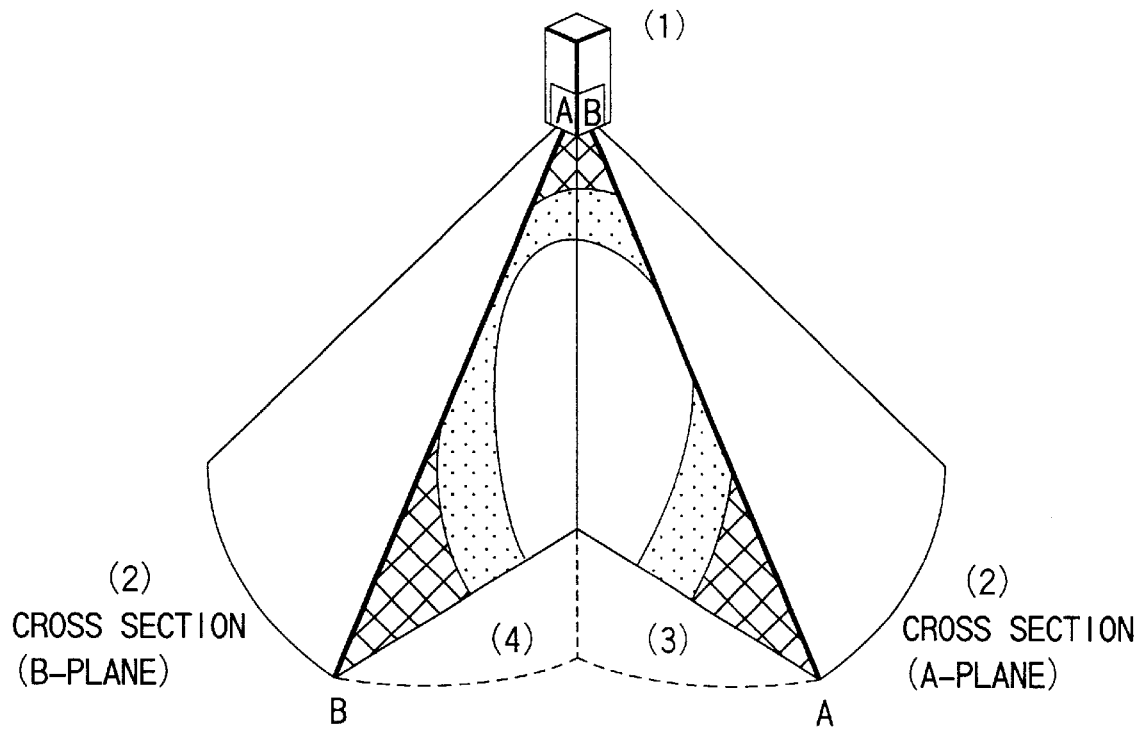
FIG. 16 shows probe marks for representing the orientations of two 2D scan plane sections with respect to the probe in the second embodiment.

FIG. 16 shows a display image in the first scan mode. The first scan mode is suitable for the purpose of providing B-mode images or CFM images of two orthogonal plane sections corresponding to orthogonal arrangements of piezoelectric elements in the 2D array probe 101. This scan is similar to conventional scanning of two orthogonal plane sections with a bi-plane probe and is an application of bi-plane probe-based scan to the 2D array probe.

The first scan mode subjects only two plane sections within a 3D region to 2D scan and is not therefore means for directly obtaining a 3D image in its original sense. The scan range is N×2 scan lines, smaller than the 3D scan range of N×M scan lines. Therefore, images can be provided which have such a high temporal resolution that the real-time operability is not much damaged and a high spatial resolution nevertheless only two plane sections are scanned.

It is therefore desirable to use the first scan mode as premeans for obtaining a 3D-like image, i.e., as a guide to the operator in positioning the probe on the human body. The outline of the procedure for executing the first scan mode will be explained below.

The operator first selects the first scan mode on the operating panel 111. A selection signal from the operating panel 111 is entered over the bus into the host CPU 110, which in turn outputs a control signal for the first scan mode to the transmitter/receiver unit 102 and the beam former unit 103. Thereby, a scan is made in the first scan mode. The host CPU 110 sends a control signal for signal processing corresponding to the first scan mode to the echo processor 104, the Doppler processor 105, the 3D processor 108, and the display unit 109 over the bus.

The echo processor 104 then produces a tissue-based ultrasonic image signal (a basic signal for B-mode image) from received echo signals. The Doppler processor 105 produces a blood-flow-based ultrasonic signal (a basic signal for CFM image) from received echo signals obtained in a sequential order of time from the same position. The 3D processor 108 performs operations of projecting 3D coordinate data referenced to the position of the probe 101 onto 2D images on the following display elements and performs transformation for image display.

The display elements include a wire frame model representing the contour of a 3D region, a tomography image of the plane section A (B-mode image or the like), a tomography image of the plane section B, and a probe graphic (including scan marks).

As for the probe graphic and the 3D-region wire frame model, transformation to projected image is performed by setting a given estimated position for the probe 1. As for the tomography images of the plane sections A and B obtained from the B-mode image basic signal and the CMF image basic signal as well, the same estimated position is used to perform transformation to projected image. The positions of the plane sections A and B are set on the basis of initial-state values in the host CPU 110.

In shifting a plane section, the operator changes the initial-state values through the operating panel 111. The display unit 109 superimposes each display element on top of the other to produce ultrasonic image data. A ultrasonic image is then displayed on the display monitor 107.

FIG. 16 shows a typical display example in the first scan mode when the left ventricle is viewed from the tip of the heart. The operator, while observing such a display as shown in FIG. 16, can move the probe 101 or shift the plane A or B to confirm that a region he or she wants to watch is covered.

[Second Scan Mode]

The second scan mode is suitable for the purpose of providing a 3D ultrasonic image of a local region (3D-ROI) forming a portion of a 3D region, more specifically, a 3D local region surrounded by the two orthogonal planes corresponding to the orthogonal arrangements of piezoelectric elements in the 2D array probe 1 set in the first scan mode.

In the second scan mode in which a 3D scan (N'×M' scan lines) is made, the real-time operability tends to become lower than in the first scan mode (N×2 scan lines) in which only two plane sections are extracted from 3D space within a human body. However, by restricting the 3D scan region to a local region of proper size (N'<N, 2<M'<M), the lowering of the real-time operability can be minimized. Above all, 3D information can be provided which is never available in the first scan mode.

Therefore, it is preferable to use the second scan mode in order to obtain a 3D image after image display in the first scan mode serving as positioning guide.

The outline of the procedure of executing the second scan mode will be described below.

The operator first switches the scan mode to this mode through the operating panel 111. The following procedure remains basically unchanged from that in the first scan mode. In this scan mode, the 3D processor 108 performs operations of projecting 3D coordinate data that is referenced to the position of the probe 101 onto 2D images on the following display elements and performs basic coordinate and size transformation processing for image display and, particularly for a 3D image, generally known 3D image reconstruction processing including: (1) setting of transparency for perspective representation, (2) maximum value projection processing called MIP, and (3) contour extraction preprocessing and volume rendering postprocessing.

The display elements include a wire frame model representing the contour of a 3D region, a 3D tomography image, and a probe graphic (including scan marks).

The probe graphic and the wire frame model for a 3D region may or may not be displayed. The operation when they are displayed remains unchanged from that in the first scan mode. The graphic of a local region subjected to a 3D scan is transformed to a projected image by setting a given estimated position for the probe.

A 3D ultrasonic image obtained from B-mode image basic signals and CFM image basic signals for a local region subjected to a 3D scan is also transformed to a projected image using the same estimated position. The setting of the estimated position is performed on the basis of the initial values in the host CPU 10. To shift the estimated position, the operator simply updates the initial values through the operating panel 111. To shift a region of interest, the operator simply performs a similar operation through the operating panel.

FIGS. 17A and 17B show a typical display example in the second scan mode for observation of the bicuspid when the left ventricle is viewed from the tip of the heart. A 3D image shown in FIG. 17B may be displayed within the 3D-ROI or may be displayed separately outside the 3D-ROI as shown in FIG. 17A. In the latter case, the 3D-ROI graphic itself serves the function of a guide for understanding the orientation and facilitates the understanding of the position of the 3D image cut out. Even if the cut 3D image has hidden portions difficult to view under the default estimated position, the estimated position can be rotated or the image itself can be enlarged by the 3D processor, thus making such portions easy to view.

The operator is allowed, while viewing such a display as shown in FIG. 17 in real time, to record moving images on video tape or to photograph a still image after scanning is frozen at an appropriate time. Since a 3D image can be provided in real time, the time and accuracy of stress echo-based diagnosis useful in examining (???) heart diseases can be improved. The reason is as follows: The conventional stress echo method, which evaluates the behavior of cardiac muscles through tomography images only, needs to record a plurality of tomography images one after another in a short time. In contrast, this inventive method allows easy positioning in the first scan mode and moreover allows an originally desired 3D-like image to be recorded in real time in the second scan mode.

[Third Scan Mode]

The third scan mode is suitable for the purpose of providing B-mode images or CFM images for two orthogonal planes corresponding to orthogonal arrangements of piezoelectric elements in the 2D array probe 101 set in the first scan mode and providing a 3D ultrasonic image for a 3D local region included in space surrounded by the two orthogonal planes. This scan mode is a hybrid of the first and second scan modes and consequently the display is also a combination of the display in the second scan mode and the display of two tomography images. For the third scan mode, there are roughly two modes of use according to the purpose.

The first mode of use mainly aims to make full use of the merits of high image quality and a large number of frames in the first scan mode. In this mode it is preferable that, after the first scan mode is carried out as a guide for positioning, the third scan mode be used to obtain a 3D-like image. For example, the first mode of use is suitable for the first medical examination when the operator has no previously obtained information concerning positioning.

In the second mode of use, the third scan mode is selectively used from the beginning with no operation of switching the scan modes. For example, the second mode is suitable for the observation of progress of the state of a human body in the case where the operator has previously obtained information concerning the human body.

The outline of the procedure of executing of the operation in the third scan mode will be explained below.

The operator first makes a transition to the third scan mode through the operating panel 111. The following operation remains basically unchanged from that in the second scan mode and description thereof is therefore omitted. In this scan mode, the 3D processor 108 performs given processing on the following display elements.

The display elements include a wire frame model representing the contour of a local region (3D-ROI), a 3D ultrasonic image, a probe graphic (including scan marks), a wire frame model for a 3D region, a tomography image of the plane section A (B-mode image or the like), and a tomography image of the plane section B.

Figures 18A, 18B:
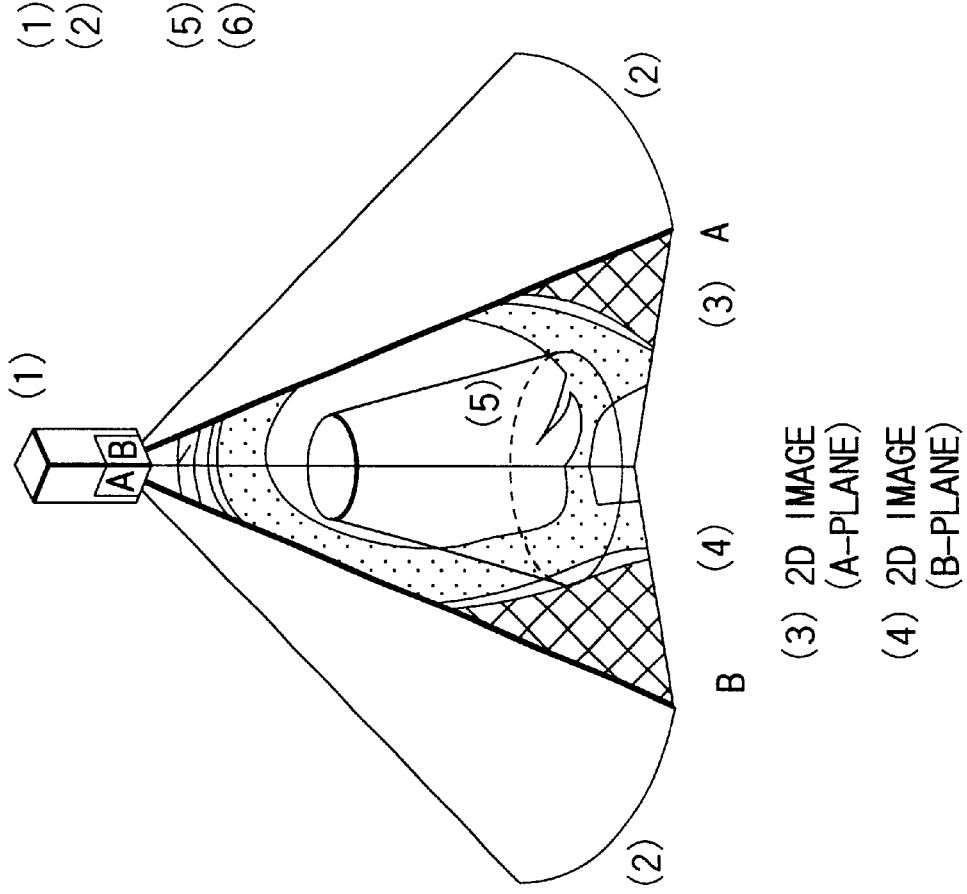
FIG. 18A shows the location map of FIG. 17A in which a 2D image is fitted.
FIG. 18B shows a 3D image displayed within the 3D scan local region in FIG. 18A.
Figure 20A:
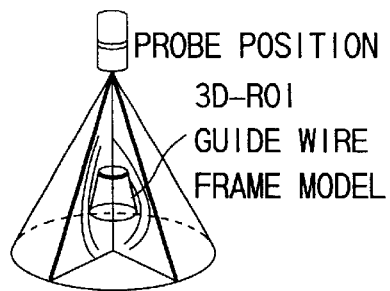
FIGS. 20A through 20F illustrate a procedure of setting the size and position of the 3D scan local region in the second embodiment.
Figure 20B:
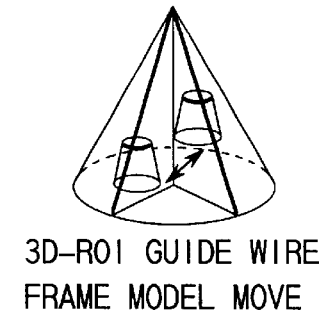
Figure 20C:
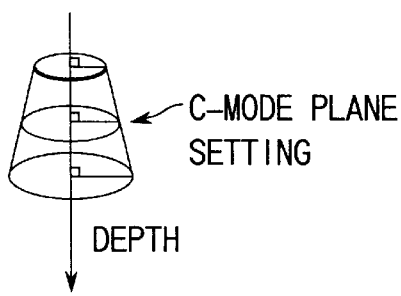
Figure 20D:
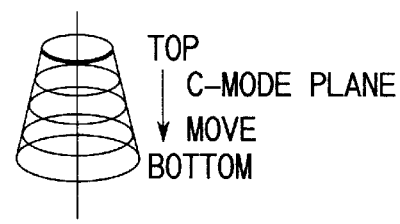
Figure 20E:
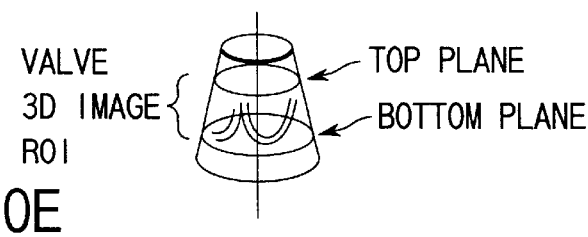
Figure 20F:
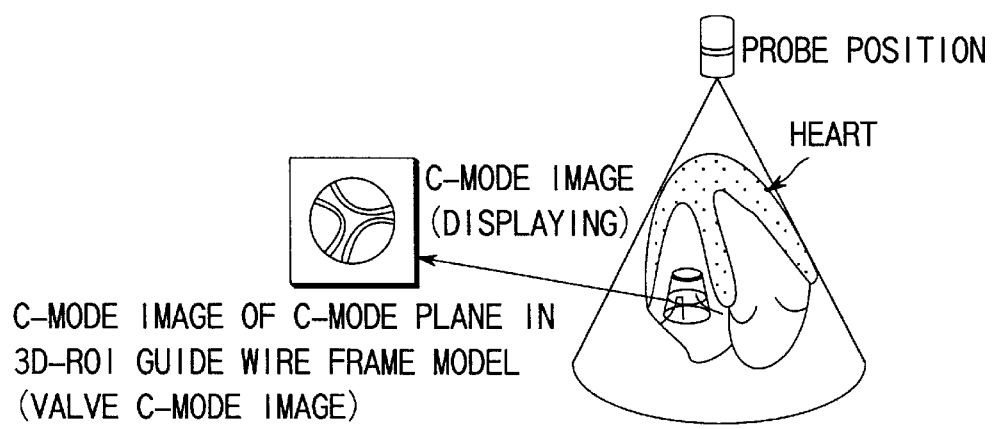

In FIGS. 18A and 18B there is illustrated a typical display example in the third scan mode for observation of the bicuspid when the left ventricle is viewed from the tip of the heart. A 3D image may be displayed within the 3D-ROI or may be displayed separately outside the 3D-ROI as shown. In the latter case, the 3D-ROI itself serves the function of a guide for understanding the orientation and facilitates the understanding of the position of the 3D image cut out. Even if the cut 3D image has hidden portions difficult to view under the default estimated position, the estimated position can be rotated or the image itself can be enlarged by the 3D processor, thus improving visibility.

When the 3D image is displayed inside the 3D-ROI, it is displayed overlapped with the two tomography images A and B in the background. To permit the tomography images and the 3D image to be observed separately, it is preferable that they be displayed with different transparency. As an example, those portions of the tomography images which are not overlapped with the 3D image are displayed usually. Those portions of the tomography images which are overlapped with the 3D image are displayed with a transparency of $\alpha$ and the 3D image is displayed with a transparency of $1-\alpha$. By so doing, even in the overlapping portions, the tomography images in the background will be displayed through the semi-transparent 3D image, making comparison in orientation between the tomography images and the 3D image easy to understand. Of course, in addition to the transparency setting, tomography image color map setting and 3D image color map setting can be made different. In that case, the tomography images and the 3D image can be observed separately with different shades of color. The color map setting can be implemented in the 3D processor 108 or the display unit 109.

The image display in the present invention is not limited to the examples described so far. Various modifications are possible.

For example, in FIG. 18, the tomography images are tissue-based B-mode images and the 3D image is a tissue-based 3D image subjected to MIP or volume rendering. The tomography images may be blood-flow-based CFM images, CFM images containing tissue motion called tissue Doppler, or B-mode images containing information dependent on the non-linearity of tissue propagation called tissue harmonic. The same is true for the 3D image.

It does not matter if a contrast medium is given to a patient and information based on the contrast medium is contained in received echo signals. This is because the present invention aims at new display procedures, display methods, and ultrasound scanning methods. As another display example in the third scan mode, a typical display example for examination of blood flow within a lever tumor is illustrated in FIGS. 19A and 19B.

In the third scan mode, it may follow from various constraints and examination purposes that there are suitable combinations and unsuitable combinations of the modes of tomography and 3D images. Particularly in the case where the heart is examined as shown in FIG. 18, the ultrasonic diagnostic apparatus is required to have real-time operability. In such a case, a combination in which the frame rates is maximized is desirable. As indicated in the accompanying sheet 1, in order to provide an appropriate frame rates for a blood flow-based 3D image, it is required to limit the size of a local region actually subjected to 3D scan or decrease the density of scan lines. A blood flow-based CFM image, even if it is a tomography image, requires the frame rates to be decreased excessively. Thus, the combination of a blood flow-based 3D image and a blood-flow-based CFM tomography image is not suitable.

In the third scan mode, where the real-time operability is taken as important, it is more desirable to consider tomography images to only function as a guide for giving the orientation of a 3D image and to display normal B-mode images.

Moreover, in the scanning sequence for tomography and 3D images, the scan ratio between the 2D scan in the first scan mode and the 3D scan in the second scan mode can be changed. For example, as shown in FIG. 21A, it is recommended to allocate more time to a scan for which temporal resolution has great weight, in addition to a general sequence in which a 2D scan for tomography image and a 3D scan for 3D image are alternated on a time-division basis. For example, if, as shown in FIGS. 21B and 21C, most of the scan time is allocated to 3D scan and 2D scan is made occasionally (or when switch control is performed), then the lowering of the real-time operability for 3D image will be minimized. Of course, the real-time operability for tomography images is lowered, but the tomography images can serve well as the function of a positioning guide. Conversely, when importance is attached to tomography images rather than a 3D image, it is only required that most of the scan time be allocated to 2D scan and 3D scan be made occasionally (or when switch control is performed) as shown in FIGS. 21D and 21E.

FIGS. 20A through 20E are diagrams for use in explanation of a method of setting a local region (3D-ROI) subjected to a 3D scan in the second and third scan modes. Here, the method will be described in terms of the case of a valve disease. In order to observe the structure and form of a valve on a 3D basis, it is required that the valve be included in a 3D-ROI. To determine the 3D-ROI more readily, a C-mode image in the halfway position in the direction of depth within the 3D-ROI guide wire is displayed separately. The C-mode plane can be set arbitrarily at any depth within the 3D-ROI guide wire according to the purpose. As is well known, the C-mode image is a tomography image in a plane (C-mode plane) substantially orthogonal to the direction of a beam of ultrasound.

When captured in the guiding C-mode image, the valve, an object of observation, will have been included in the 3D-ROI guide wire. Thus, if a C-mode plane is set in a 3D-ROI guide wire and the guide wire is moved in real time to a scan region using a C-mode image displayed in a separate area as a guide, the 3D-ROI including the valve captured in the C-mode image can be positioned efficiently and surely. This facilitates the setting of an ROI, allowing diagnosis to proceed smoothly.

Alternatively, it is also possible to place the 3D-ROI in a region where a valve will probably be present and shift automatically or manually the C-mode plane up or down. In this case, at the time when the valve is captured well in the C-mode image, the stop position is specified by switch control and then the 3D-ROI guide wire is shifted to conform to the C-mode plane.

After the 3D-ROI has been set, the C-mode plane is newly shifted up and down to mark upper and lower limits on the 3D display region. This is useful in extracting and displaying only a certain part, a valve in this example, in a region determined by the 3D-ROI guide wire. This is more efficient than simply adjusting repeatedly the height of the 3D-ROI guide wire on the basis of the 3D displayed image so that the valve is successfully captured in the displayed region.

Alternatively, the 3D-ROI may be determined in accordance with the following procedure. First, the whole of a scan region is displayed in the form of a C-mode image. A valve which is an object of observation is captured, the stop position is designated by switch control, and a 3D-ROI guide wire of appropriate size then appears to conform to a C-mode plane. The optimum position of the 3D-ROI guide wire is determined by parallel shifting it in the C-mode plane and then its height and width are determined so that a desired 3D image display is obtained.

In addition to being merely used as the 3D-ROI setting guide, the C-mode image may be displayed simultaneously with a 3D transmissive display (MIP or integral display) of the 3D-ROI. In this case, it becomes possible to observe the motion of the entire valve on the 3D display and, at the same time, observe the motion of the valve in a specific plane through the C-mode image.

The C-mode image may be displayed not only in black and white but in colors. A C-mode color image can be used for blood flow rate measurement.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A three-dimensional ultrasonic diagnostic apparatus comprising:
   a two-dimensional array type of ultrasonic probe;
   a beam former unit for selectively performing through the piezoelectric probe a three-dimensional scan operation of scanning a three-dimensional region within a human body under examination with ultrasound and a two-dimensional scan operation of scanning a two-dimensional plane section within the three-dimensional region with ultrasound;
   a controller for controlling the beam former unit in such a way that the three-dimensional scan operation is repeated intermittently and the two-dimensional scan operation is repeated during an interval between each three-dimensional scan operation;
   an image processing unit for producing three-dimensional ultrasonic image data concerning the three-dimensional region on the basis of received signals obtained by the three-dimensional scan operation and two-dimensional ultrasonic image data concerning the two-dimensional plane section on the basis of received signals obtained by the two-dimensional scan operation; and a display unit for displaying the three-dimensional ultrasonic image data and the two-dimensional ultrasonic image data.

2. The three-dimensional ultrasonic diagnostic apparatus according to claim 1, wherein the image processing unit produces two-dimensional ultrasonic image data concerning the two-dimensional plane section on the basis of a part of received signals obtained by the three-dimensional scan operation.

3. The three-dimensional ultrasonic diagnostic apparatus according to claim 1, wherein the display unit includes means for delaying the display of the two-dimensional ultrasonic image data by the time which elapses between the moment that the three-dimensional scan operation is terminated and the moment that the three-dimensional ultrasonic image data is produced.

4. The three-dimensional ultrasonic diagnostic apparatus according to claim 1, wherein the cycle of the three-dimensional scan operation is set to the time which elapses between the moment that the three-dimensional scan operation is terminated and the moment that the three-dimensional ultrasonic image data is produced.

5. The three-dimensional ultrasonic diagnostic apparatus according to claim 1, wherein the display unit for superimposing the two-dimensional ultrasonic image data upon the three-dimensional ultrasonic image data according to the position of the two-dimensional plane section relative to the three-dimensional region.

6. The three-dimensional ultrasonic diagnostic apparatus according to claim 1, wherein the two-dimensional plane section is initially set substantially at the center of the three-dimensional region.

7. The three-dimensional ultrasonic diagnostic apparatus according to claim 6, further comprising an input device for changing the position and orientation of the two-dimensional plane section.

8. The three-dimensional ultrasonic diagnostic apparatus according to claim 7, wherein the image processing unit includes means for shifting the point of view for the three-dimensional ultrasonic image data onto the normal that passes through the center of the two-dimensional plane section having its position and orientation changed by the input device.

9. The three-dimensional ultrasonic diagnostic apparatus according to claim 1, wherein the beam former unit changes the position of the three-dimensional region scanned by the three-dimensional scan operation for each three-dimensional scan operation, and the image processing unit produces three-dimensional ultrasonic image data concerning an enlarged three-dimensional region on the basis of received signals obtained by a plurality of successive three-dimensional scan operations.

10. The three-dimensional ultrasonic diagnostic apparatus according to claim 9, wherein the image processing unit produces three-dimensional ultrasonic image data concerning the enlarged three-dimensional region in succession at the period of the three-dimensional scan operation.

11. A three-dimensional ultrasonic diagnostic apparatus comprising:

a two-dimensional array type of ultrasonic probe;

a transmitter/receiver circuit for allowing the ultrasonic probe to scan selectively a three-dimensional region within a human body under examination and a two-dimensional plane section within the three-dimensional region with ultrasound;

a controller for controlling the transmitter/receiver circuit so that a plurality of two-dimensional plane sections are scanned within the three-dimensional region;

an echo processor responsive to received signals from the transmitter/receiver circuit for producing two-dimensional ultrasonic image data for each of the plurality of two-dimensional plane sections;

a 3D processor for combining the two-dimensional ultrasonic image data for the plurality of two-dimensional plane sections according to the positions of the respective two-dimensional plane sections within the three-dimensional region to produce composite two-dimensional ultrasonic image data; and a display unit for displaying the composite two-dimensional ultrasonic image data.

12. The three-dimensional ultrasonic diagnostic apparatus according to claim 11, wherein the 3D processor further combines three-dimensional graphic data representing the contour of the three-dimensional region with the composite two-dimensional ultrasonic image data according to the position of each of the plurality of two-dimensional plane sections within the three-dimensional region.

13. The three-dimensional ultrasonic diagnostic apparatus according to claim 11, further comprising an input device for setting each of the two-dimensional plane sections to have any arbitrary position and orientation within the three-dimensional region.

14. The three-dimensional ultrasonic diagnostic apparatus according to claim 11, wherein the controller controls the transmitter/receiver circuit to scan a three-dimensional local region within the three-dimensional region as well as the plurality of two-dimensional plane sections, and the 3D processor produces three-dimensional ultrasonic image data concerning the three-dimensional local region on the basis of received signals obtained by the transmitter/receiver circuit.

15. The three-dimensional ultrasonic diagnostic apparatus according to claim 14, wherein the 3D processor combines the three-dimensional ultrasonic image data with the composite two-dimensional ultrasonic image data according to the position of the three-dimensional local region within the three-dimensional region.

16. The three-dimensional ultrasonic diagnostic apparatus according to claim 14, wherein the 3D processor combines three-dimensional graphic data representing the contour of the three-dimensional region with the three-dimensional ultrasonic image data and the composite two-dimensional ultrasonic image data according to the position of the three-dimensional local region and the position of each of the two-dimensional plane sections within the three-dimensional region.

17. The three-dimensional ultrasonic diagnostic apparatus according to claim 11, wherein the plurality of two-dimensional plane sections are set to meet on the central axis of the three-dimensional region.

18. The three-dimensional ultrasonic diagnostic apparatus according to claim 11, wherein the controller controls the transmitter/receiver circuit to shift at least one of the plurality of two-dimensional plane sections in the three-dimensional region.

19. The three-dimensional ultrasonic diagnostic apparatus according to claim 11, wherein the 3D processor combines three-dimensional graphic data representing the orientation of the ultrasonic probe with the composite two-dimensional ultrasonic image data.

20. The three-dimensional ultrasonic diagnostic apparatus according to claim 11, further comprising an input device for setting the three-dimensional local region in any arbitrary position and size within the three-dimensional region.

21. The three-dimensional ultrasonic diagnostic apparatus according to claim 20, wherein the 3D processor produces C-mode image data concerning a plane section orthogonal to the central axis of the three-dimensional region on the basis of received signals from the transmitter/receiver circuit to support the setting of the three-dimensional local region.

22. The three-dimensional ultrasonic diagnostic apparatus according to claim 21, wherein the 3D processor automatically shifts the plane section for which the C-mode image data is produced up and down along the central axis of the three-dimensional region.

23. A three-dimensional ultrasonic diagnostic apparatus comprising:

a two-dimensional array probe in which a plurality of ultrasonic transducer elements are arranged in the form of a two-dimensional array;

driving means for causing the two-dimensional array probe to make intermittently a three-dimensional scan of an objective region and causing the two-dimensional array probe to make a two-dimensional scan at a frame rate higher than a volume rate of the tree-dimensional scan during the interval between each three-dimensional scan; and image producing means responsive to ultrasonic information obtained by the three-dimensional and two-dimensional scans for producing ultrasonic images.

24. The three-dimensional ultrasonic diagnostic apparatus according to claim 23, wherein the scanning density of the two-dimensional scan is higher than that of the three-dimensional scan.

25. The three-dimensional ultrasonic diagnostic apparatus according to claim 23, wherein the three-dimensional and two-dimensional scans each include simultaneous parallel reception for forming ultrasound echo signals for a plurality of scan lines on the basis of ultrasound received signal obtained for each transmission of ultrasound, the number of simultaneous parallel receptions in the two-dimensional scan being smaller than that in the three-dimensional scan.

26. The three-dimensional ultrasonic diagnostic apparatus according to claim 23, wherein the three-dimensional scan includes simultaneous parallel reception for forming ultrasound echo signals for a plurality of scan lines on the basis of ultrasound received signal obtained for each transmission of ultrasound, and the two-dimensional scan does not.

\* \* \* \* \*